(12) United States Patent
Petkovich et al.

(10) Patent No.: US 10,302,660 B2
(45) Date of Patent: *May 28, 2019

(54) METHODS USEFUL FOR VITAMIN D DEFICIENCY AND RELATED DISORDERS

(71) Applicants: OPKO RENAL, LLC, Miami, FL (US); OPKO IRELAND GLOBAL HOLDINGS, LTD., Grand Cayman (KY)

(72) Inventors: P. Martin Petkovich, Kingston (CA); Christian F. Helvig, Markham (CA); Joel Z. Melnick, Wilmette, IL (US)

(73) Assignees: OPKO RENAL, LLC, Miami, FL (US); OPKO IRELAND GLOBAL HOLDINGS, LTD., Grand Cayman (KY)

(*) Notice: Subject to any disclaimer, the term of this patent is extended or adjusted under 35 U.S.C. 154(b) by 0 days.

This patent is subject to a terminal disclaimer.

(21) Appl. No.: 15/357,059

(22) Filed: Nov. 21, 2016

(65) Prior Publication Data

US 2017/0067917 A1    Mar. 9, 2017

Related U.S. Application Data

(60) Continuation of application No. 14/607,725, filed on Jan. 28, 2015, now Pat. No. 9,500,661, which is a division of application No. 12/935,139, filed as application No. PCT/US2009/039355 on Apr. 2, 2009, now Pat. No. 8,962,239.

(60) Provisional application No. 61/161,292, filed on Mar. 18, 2009, provisional application No. 61/041,898, filed on Apr. 2, 2008.

(51) Int. Cl.

| | | |
|---|---|---|
| *G01N 33/53* | (2006.01) | |
| *G01N 33/573* | (2006.01) | |
| *A01N 45/00* | (2006.01) | |
| *G01N 33/82* | (2006.01) | |
| *A61K 31/00* | (2006.01) | |
| *A61K 45/06* | (2006.01) | |
| *C12Q 1/68* | (2018.01) | |
| *G01N 33/68* | (2006.01) | |
| *A61K 31/592* | (2006.01) | |
| *A61K 31/593* | (2006.01) | |
| *C12Q 1/6883* | (2018.01) | |
| *C12Q 1/6876* | (2018.01) | |
| *A61K 31/59* | (2006.01) | |

(52) U.S. Cl.
CPC ............ *G01N 33/82* (2013.01); *A61K 31/00* (2013.01); *A61K 31/59* (2013.01); *A61K 31/592* (2013.01); *A61K 31/593* (2013.01); *A61K 45/06* (2013.01); *C12Q 1/6876* (2013.01); *C12Q 1/6883* (2013.01); *G01N 33/6893* (2013.01); *C12Q 2600/106* (2013.01); *C12Q 2600/158* (2013.01); *G01N 2333/50* (2013.01); *G01N 2333/90251* (2013.01); *G01N 2800/04* (2013.01); *G01N 2800/046* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 3,565,924 | A | 2/1971 | DeLuca et al. |
| 3,833,622 | A | 9/1974 | Babcock et al. |
| 3,880,894 | A | 4/1975 | De Luca et al. |
| 4,004,003 | A | 1/1977 | Babcock et al. |
| 4,230,701 | A | 10/1980 | Holick et al. |
| 4,335,120 | A | 6/1982 | Holick et al. |
| 4,448,721 | A | 5/1984 | DeLuca et al. |
| 4,555,364 | A | 11/1985 | DeLuca et al. |
| 4,668,517 | A | 5/1987 | Weber et al. |
| 4,684,524 | A | 8/1987 | Eckenhoff et al. |
| 4,695,591 | A | 9/1987 | Hanna et al. |
| 4,721,613 | A | 1/1988 | Urquhart et al. |

(Continued)

FOREIGN PATENT DOCUMENTS

| | | |
|---|---|---|
| CA | 2241205 A1 | 7/1997 |
| EP | 0 227 836 A1 | 7/1987 |

(Continued)

OTHER PUBLICATIONS

"Hidroferol® (calcifediol): Casos de Hipercalcemia e Hipervitaminosis D," Butlletí de Farmacovigilància de Catalunya, 9(5):17-20 (2011).
"Modern Pharmaceutics" 4th ed., Marcel Dekker, Inc., New York, NY, p. 16-21 (2002).
Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).
Alvarez et al., "Vitamin D Supplementation in Pre-Dialysis Chronic Kidney Disease," *Dermato-Endocrinology*, 4(2):118-127 (2012).
Anderson et al., Quantification of mRNA for the vitamin D metabolizing enzymes CYP27B1 and CYP24 and vitamin D receptor in kidney using real-time reverse transcriptase-polymerase chain reaction, 2003. J. Mol. Endoc 31:123-132.

(Continued)

*Primary Examiner* — Shulamith H Shafer
(74) *Attorney, Agent, or Firm* — Marshall, Gerstein & Borun LLP

(57) ABSTRACT

Methods for diagnosing, treating, and preventing catabolism-related vitamin D deficiency and related disorders, related compositions, apparatus and kits, are disclosed. A method involves measuring CYP24 expression and/or activity, or a proxy thereof such as FGF23 level, in a patient and correlating abnormally elevated CYP24 expression and/or activity with catabolism-related vitamin D deficiency or with susceptibility for catabolism-related vitamin D deficiency. In response to abnormally elevated CYP24 expression and/or activity, the method further includes administering a CYP24 inhibitor to the vitamin D deficient or at-risk patient, and preferably avoiding activation of the vitamin D binding receptor, such as by avoiding administration of active vitamin D compounds to such patients. Optionally, a vitamin D prohormone or prohormone can be administered.

37 Claims, 19 Drawing Sheets

(56) References Cited

U.S. PATENT DOCUMENTS

| | | | |
|---|---|---|---|
| 4,729,895 A | 3/1988 | Makino et al. | |
| 4,755,544 A | 7/1988 | Makino et al. | |
| 4,892,821 A | 1/1990 | Omura et al. | |
| 4,997,824 A | 3/1991 | Popovtzer et al. | |
| 5,026,559 A | 6/1991 | Eichel et al. | |
| 5,160,742 A | 11/1992 | Mazer et al. | |
| 5,328,903 A | 7/1994 | Ishii et al. | |
| 5,342,626 A | 8/1994 | Winston, Jr. et al. | |
| 5,354,743 A | 10/1994 | Thys-Jacobs | |
| 5,403,831 A | 4/1995 | DeLuca et al. | |
| 5,431,917 A | 7/1995 | Yamamoto et al. | |
| 5,472,712 A | 12/1995 | Oshlack et al. | |
| 5,487,900 A | 1/1996 | Itoh et al. | |
| 5,529,991 A | 6/1996 | Knutson et al. | |
| 5,593,690 A | 1/1997 | Akiyama et al. | |
| 5,602,116 A | 2/1997 | Knutson et al. | |
| 5,614,513 A | 3/1997 | Knutson et al. | |
| 5,622,941 A | 4/1997 | Knutson et al. | |
| 5,693,615 A | 12/1997 | Stone | |
| 5,707,980 A | 1/1998 | Knutson et al. | |
| 5,756,123 A | 5/1998 | Yamamoto et al. | |
| 5,783,215 A | 7/1998 | Arwidsson et al. | |
| 5,795,882 A | 8/1998 | Bishop et al. | |
| 5,861,386 A | 1/1999 | Knutson et al. | |
| 5,869,473 A | 2/1999 | Knutson et al. | |
| 5,958,451 A | 9/1999 | Chen | |
| 6,034,075 A | 3/2000 | Thys-Jacobs | |
| 6,051,567 A | 4/2000 | Abrahamson et al. | |
| 6,096,876 A | 8/2000 | St-Arnaud et al. | |
| 6,121,469 A | 9/2000 | Norman et al. | |
| 6,133,250 A | 10/2000 | Knutson et al. | |
| 6,139,875 A | 10/2000 | Adams et al. | |
| 6,147,064 A | 11/2000 | Knutson et al. | |
| 6,150,346 A | 11/2000 | Knutson et al. | |
| 6,190,591 B1 | 2/2001 | van Lengerich | |
| 6,190,695 B1 | 2/2001 | Hoshino et al. | |
| 6,214,376 B1 | 4/2001 | Gennadios | |
| 6,228,849 B1 | 5/2001 | Thys-Jacobs | |
| 6,242,434 B1 | 6/2001 | Bishop et al. | |
| 6,265,392 B1 | 7/2001 | Abrahamson et al. | |
| 6,274,169 B1 | 8/2001 | Abrahamson et al. | |
| 6,288,849 B1 | 9/2001 | Teramoto | |
| 6,340,473 B1 | 1/2002 | Tanner et al. | |
| 6,342,249 B1 | 1/2002 | Wong et al. | |
| 6,375,981 B1 | 4/2002 | Gilleland et al. | |
| 6,376,479 B1 | 4/2002 | Knutson et al. | |
| 6,380,408 B1 | 4/2002 | Posner et al. | |
| 6,413,463 B1 | 7/2002 | Yamamoto et al. | |
| 6,432,936 B1 | 8/2002 | DeLuca et al. | |
| 6,491,950 B1 * | 12/2002 | Gutierrez-Rocca | A61K 9/4858 424/451 |
| 6,503,893 B2 | 1/2003 | Bishop et al. | |
| 6,521,608 B1 | 2/2003 | Henner et al. | |
| 6,524,788 B1 | 2/2003 | Cantor | |
| 6,569,463 B2 | 5/2003 | Patel et al. | |
| 6,572,888 B2 | 6/2003 | Byrd | |
| 6,582,727 B2 | 6/2003 | Tanner et al. | |
| 6,596,314 B2 | 7/2003 | Wong et al. | |
| 6,770,295 B1 | 8/2004 | Kreilgard et al. | |
| 6,893,658 B1 | 5/2005 | Iida et al. | |
| 6,903,083 B2 | 6/2005 | Knutson et al. | |
| 6,911,217 B1 | 6/2005 | Gren et al. | |
| 6,923,988 B2 | 8/2005 | Patel et al. | |
| 6,929,803 B2 | 8/2005 | Wong et al. | |
| 6,949,256 B2 | 9/2005 | Fonkwe et al. | |
| 6,982,258 B2 | 1/2006 | Posner et al. | |
| RE39,079 E | 4/2006 | Tanner et al. | |
| 7,033,996 B2 | 4/2006 | Christakos | |
| 7,056,655 B2 | 6/2006 | Cantor | |
| 7,101,865 B2 | 9/2006 | Posner et al. | |
| 7,122,530 B2 | 10/2006 | Bishop et al. | |
| 7,166,585 B2 | 1/2007 | Posner et al. | |
| 7,189,843 B2 | 3/2007 | Tsai et al. | |
| 7,226,932 B2 | 6/2007 | Gokhale et al. | |
| 7,255,921 B2 | 8/2007 | Kamaguchi et al. | |
| 7,422,758 B2 | 9/2008 | Block et al. | |
| 7,632,518 B2 | 12/2009 | Tritsch et al. | |
| 7,648,826 B1 | 1/2010 | Albertson et al. | |
| 7,807,194 B2 | 10/2010 | Modliszewski et al. | |
| 7,816,341 B2 | 10/2010 | Sewall et al. | |
| 7,846,475 B2 | 12/2010 | Shiraishi et al. | |
| 7,973,024 B2 * | 7/2011 | Posner | C07C 401/00 514/167 |
| 8,088,410 B2 | 1/2012 | Tritsch et al. | |
| 8,101,203 B2 | 1/2012 | Cao | |
| 8,101,204 B2 | 1/2012 | Cao | |
| 8,142,811 B2 | 3/2012 | Oshlack et al. | |
| 8,207,149 B2 | 6/2012 | Tabash et al. | |
| 8,231,896 B2 | 7/2012 | Tanner et al. | |
| 8,268,352 B2 | 9/2012 | Vaya et al. | |
| 8,293,270 B2 | 10/2012 | Sukuru | |
| 8,361,488 B2 | 1/2013 | Bishop et al. | |
| 8,377,470 B2 | 2/2013 | Tanner et al. | |
| 8,426,391 B2 | 4/2013 | Bishop et al. | |
| 8,759,328 B2 | 6/2014 | Deluca et al. | |
| 8,778,373 B2 | 7/2014 | Bishop et al. | |
| 8,906,410 B2 | 12/2014 | Bishop et al. | |
| 8,962,239 B2 | 2/2015 | Petkovich et al. | |
| 8,992,971 B2 | 3/2015 | Yang | |
| 9,017,720 B2 | 4/2015 | Andersen et al. | |
| 9,500,661 B2 | 11/2016 | Petkovich et al. | |
| 2001/0028896 A1 | 10/2001 | Byrd | |
| 2001/0036472 A1 | 11/2001 | Wong et al. | |
| 2002/0018810 A1 | 2/2002 | Oshlack et al. | |
| 2002/0031798 A1 | 3/2002 | Anazawa et al. | |
| 2002/0044968 A1 | 4/2002 | van Lengerich | |
| 2002/0081331 A1 | 6/2002 | Tanner et al. | |
| 2002/0128240 A1 | 9/2002 | Mazess | |
| 2002/0155154 A1 | 10/2002 | Wong et al. | |
| 2002/0183288 A1 | 12/2002 | Mazess et al. | |
| 2003/0059471 A1 | 3/2003 | Compton et al. | |
| 2003/0129194 A1 | 7/2003 | Mazess et al. | |
| 2003/0138482 A1 | 7/2003 | Fonkwe et al. | |
| 2003/0157560 A1 | 8/2003 | Cantor | |
| 2004/0043971 A1 | 3/2004 | Mazess et al. | |
| 2004/0101554 A1 | 5/2004 | Kirschner et al. | |
| 2004/0224930 A1 | 11/2004 | Posner et al. | |
| 2005/0014211 A1 | 1/2005 | Armbruster et al. | |
| 2005/0019374 A1 | 1/2005 | Modliszewski et al. | |
| 2005/0037064 A1 | 2/2005 | Basquin et al. | |
| 2005/0069579 A1 | 3/2005 | Kamaguchi et al. | |
| 2005/0101576 A1 | 5/2005 | Whitehouse et al. | |
| 2005/0106233 A1 | 5/2005 | Andersen et al. | |
| 2005/0124591 A1 | 6/2005 | Tian et al. | |
| 2005/0143358 A1 | 6/2005 | DeLuca et al. | |
| 2005/0148557 A1 | 7/2005 | Tian et al. | |
| 2005/0148558 A1 | 7/2005 | Knutson et al. | |
| 2005/0186268 A1 | 8/2005 | Hoshi et al. | |
| 2005/0208055 A1 | 9/2005 | Chuang et al. | |
| 2005/0287213 A1 | 12/2005 | Wong et al. | |
| 2006/0009425 A1 | 1/2006 | Delgado-Herrera et al. | |
| 2006/0019933 A1 | 1/2006 | Boardman et al. | |
| 2006/0029660 A1 | 2/2006 | Fonkwe et al. | |
| 2006/0034937 A1 | 2/2006 | Patel | |
| 2006/0193877 A1 | 8/2006 | Tengler et al. | |
| 2006/0210610 A1 | 9/2006 | Davidson et al. | |
| 2006/0223119 A1 | 10/2006 | Cantor | |
| 2006/0228808 A1 | 10/2006 | Clarke et al. | |
| 2006/0257481 A1 | 11/2006 | Gurney et al. | |
| 2007/0026067 A1 | 2/2007 | Yam et al. | |
| 2007/0122477 A1 | 5/2007 | Bishop et al. | |
| 2007/0190146 A1 | 8/2007 | Roger et al. | |
| 2007/0207488 A1 | 9/2007 | Trump et al. | |
| 2008/0109983 A1 | 5/2008 | Davis | |
| 2008/0134937 A1 | 6/2008 | Yang | |
| 2008/0317764 A1 | 12/2008 | Huber et al. | |
| 2009/0004284 A1 | 1/2009 | Cheng et al. | |
| 2009/0069389 A1 | 3/2009 | Choi et al. | |
| 2009/0137536 A1 | 5/2009 | Mazess et al. | |
| 2009/0155355 A1 | 6/2009 | Heuer et al. | |
| 2009/0176748 A1 | 7/2009 | Tabash et al. | |
| 2009/0311316 A1 | 12/2009 | Bishop et al. | |
| 2010/0144684 A1 | 6/2010 | Bishop | |

(56) References Cited

U.S. PATENT DOCUMENTS

| | | |
|---|---|---|
| 2010/0291197 A1 | 11/2010 | Schwab |
| 2011/0039810 A1 | 2/2011 | Buck et al. |
| 2011/0039811 A1 | 2/2011 | Buck et al. |
| 2011/0105444 A1 | 5/2011 | Deluca et al. |
| 2011/0118218 A1 | 5/2011 | Buck et al. |
| 2011/0171298 A1 | 7/2011 | Cao |
| 2011/0182986 A1 | 7/2011 | Speirs et al. |
| 2011/0256230 A1 | 10/2011 | Haeusler et al. |
| 2011/0300210 A1 | 12/2011 | Swanson et al. |
| 2011/0319503 A1 | 12/2011 | Muller et al. |
| 2012/0015916 A1* | 1/2012 | Tabash ............... A61K 9/4858 514/167 |
| 2013/0189522 A1 | 7/2013 | Fujii et al. |
| 2013/0216618 A1 | 8/2013 | Muller et al. |
| 2013/0302309 A1 | 11/2013 | Yang |
| 2014/0088202 A1 | 3/2014 | Cade et al. |
| 2014/0248400 A1 | 9/2014 | Phonchareon et al. |
| 2015/0119472 A1 | 4/2015 | Shuai et al. |
| 2015/0119473 A1 | 4/2015 | Shuai et al. |

FOREIGN PATENT DOCUMENTS

| | | |
|---|---|---|
| EP | 0 508 756 A1 | 10/1992 |
| EP | 0 387 808 B1 | 5/1993 |
| EP | 0629405 A1 | 12/1994 |
| EP | 1208843 A1 | 5/2002 |
| EP | 1 165 061 B1 | 10/2005 |
| EP | 2 148 661 B1 | 12/2012 |
| JP | 58-032823 | 2/1983 |
| JP | S58206524 A | 12/1983 |
| JP | 04-208225 A | 7/1992 |
| JP | H04288016 A | 10/1992 |
| JP | 07-242550 A | 9/1995 |
| JP | 08-092098 A | 4/1996 |
| JP | 10-158171 A | 6/1998 |
| JP | 2001-512418 A | 8/2001 |
| JP | 2002302447 A | 10/2002 |
| JP | 2004-175750 A | 6/2004 |
| JP | 2005-513419 A | 5/2005 |
| JP | 2010-506520 A | 2/2010 |
| WO | WO-91/012807 A1 | 9/1991 |
| WO | WO-91/016899 A1 | 11/1991 |
| WO | WO-94/000128 A1 | 1/1994 |
| WO | WO-96/000074 A1 | 1/1996 |
| WO | WO-96/001621 A1 | 1/1996 |
| WO | WO-96/031215 A1 | 10/1996 |
| WO | WO-97/011053 A1 | 3/1997 |
| WO | WO-98/018610 A1 | 5/1998 |
| WO | WO-98/029105 A2 | 7/1998 |
| WO | WO-99/011272 A1 | 3/1999 |
| WO | WO-00/021504 A1 | 4/2000 |
| WO | WO-00/035419 A2 | 6/2000 |
| WO | WO-00/60109 A1 | 10/2000 |
| WO | WO-00/061123 A2 | 10/2000 |
| WO | WO-01/037808 A1 | 5/2001 |
| WO | WO-03/039521 A1 | 5/2003 |
| WO | WO-03/039572 A1 | 5/2003 |
| WO | WO-03/045381 A1 | 6/2003 |
| WO | WO-03/047595 A1 | 6/2003 |
| WO | WO-03/088976 A1 | 10/2003 |
| WO | WO-03/093459 A1 | 11/2003 |
| WO | WO-2004/028515 A1 | 4/2004 |
| WO | WO-2004/058235 A2 | 7/2004 |
| WO | WO-2004/080467 A2 | 9/2004 |
| WO | WO-2004/101554 A1 | 11/2004 |
| WO | WO-2004/110381 A2 | 12/2004 |
| WO | WO-2005/000268 A2 | 1/2005 |
| WO | WO-2005/003358 A1 | 1/2005 |
| WO | WO-2005/011652 A2 | 2/2005 |
| WO | WO-2005/123120 A1 | 12/2005 |
| WO | WO-2006/052452 A1 | 5/2006 |
| WO | WO-2006/059180 A2 | 6/2006 |
| WO | WO-2006/113505 A2 | 10/2006 |
| WO | WO-2007/039193 A1 | 4/2007 |
| WO | WO-2007/039569 A2 | 4/2007 |
| WO | WO-2007/047327 A2 | 4/2007 |
| WO | WO-2007/050724 A2 | 5/2007 |
| WO | WO-2007/050975 A2 | 5/2007 |
| WO | WO-2007/053608 A2 | 5/2007 |
| WO | WO-2007/068287 A1 | 6/2007 |
| WO | WO-2007/092221 A2 | 8/2007 |
| WO | WO-2007/092755 A2 | 8/2007 |
| WO | WO-2007/146004 A1 | 12/2007 |
| WO | WO-2008/008608 A2 | 1/2008 |
| WO | WO-2008/043449 A1 | 4/2008 |
| WO | WO-2008/097646 A1 | 8/2008 |
| WO | WO-2008/134512 A1 | 11/2008 |
| WO | WO-2008/134523 A1 | 11/2008 |
| WO | WO-2009/047644 A2 | 4/2009 |
| WO | WO-2009/101132 A1 | 8/2009 |
| WO | WO-2009/101137 A1 | 8/2009 |
| WO | WO-2010/011906 A1 | 1/2010 |
| WO | WO-2010/034342 A1 | 4/2010 |
| WO | WO-2011/031621 A2 | 3/2011 |
| WO | WO-2011/095388 A1 | 8/2011 |
| WO | WO-2012/018329 A1 | 2/2012 |
| WO | WO-2012/076429 A1 | 6/2012 |
| WO | WO-2012/091569 A1 | 7/2012 |
| WO | WO-2012/117236 A1 | 9/2012 |
| WO | WO-2014/202754 A1 | 12/2014 |

OTHER PUBLICATIONS

Andress, "Vitamin D in chronic kidney disease: A systematic role for selective vitamin D receptor activation," Kidney Int., 69:33-43 (2006).

Arekat et al., "Dramatic Improvement of BMD Following Vitamin D Therapy in a Bone Marrow Transplant Recipient," J. Clin. Densitometry, 5:267-271 (2002).

Armas et al., "Vitamin $D_2$ is Much Less Effective than Vitamin $D_3$ in Humans," J. Clin. Endocrinol. Metab., 89:5387-5391 (2004).

Bagnis et al., "Biochemical and Hormonal Short-Term Effects of 25-hydroxyvitamin D3 in Patients on Continuous Peritoneal Dialysis," Ital. J. Mineral Electrolyte Metab., 12:73-76 (1998).

Bailie et al. "Comparative Review of the Pharmacokinetics of Vitamin D Analogues," Seminars in Dialysis, 15(5):352-357 (2000).

Baird et al., "Steroid Dynamics Under Steady-State Conditions," Recent Prog. Horm. Res., 25:611-664 (1969).

Barger-Lux M.J. et al., "Vitamin D and Its Major Metabolites: Serum Levels After Graded Oral Dosing in Healthy Men" Osteoporosis International, United Kingdom, 8(3):222-230 (1998).

Barreto et al., "25-Hydroxyvitamin $D_3$, the Prohormone of 1,25-Dihydroxyvitamin $D_3$, Inhibits the Proliferation of Primary Prostatic Epithelial Cells," Cancer Epidemiol, Biomarkers & Prevention, 9:265-270 (2000).

Beckman, et al., "Up-Regulation of the Intestinal 1, 25-Dihydroxyvitamin D Receptor During Hypervitaminosis D: A Comparison Between Vitamin D2 and Vitamin D31," Biochemical and Biophysical Research Communications, vol. 169, No. 3, pp. 910-915 (Jun. 29, 1990).

Beer et al., "Pharmacokinetics and Tolerability of a Single Dose of DN-101, a New Formulation of Calcitriol, in Patients with Cancer," Clin. Cancer Res., 11:7794-7799 (2005).

Bell et al., "Evidence that 1,25-Dihydroxyvitamin D3 Inhibits the Hepatic Production of 25-Hydroxyvitamin D in Man," J. Clin. Invest., 74:1540-1544 (1984).

Belostotsky et al., "A single high dose of ergocalciferol can be used to boost 25-hydroxyvitamin D levels in children with kidney disease," Pediatr Nephrol, 24:625-626 (2009).

Bianchi et al., "No Difference in Intestinal Strontium Absorption After an Oral or an Intravenous 1,25(OH)2D3 Bolus in Normal Subjects," J. Bone Miner. Res., 14:1789-1795 (1999).

Binkley et al., "Laboratory Reporting of 25-Hydroxyvitamin D Results: Potential for Clinical Misinterpretation," Clinical Chemistry, 52(11);2124-2125 (2006).

Blair et al., "Prevalence of vitamin D [25(OH)D] deficiency and effects of supplementation with ergocalciferol (vitamin D2) in stage 5 chronic kidney disease patients." J.Ren Nutr., 18: 375-382 (2008).

(56) References Cited

OTHER PUBLICATIONS

Bordier et al., "Evolution of renal osteodystrophy: Correlation of bone histomorphometry and serum mineral and immunoreactive parathyroid hormone values before and after treatment with calcium carbonate or 25-hydroxycholecalciferol," *Kidney Int Suppl*, 2:S102-S112 (1975).

Boudville et al., "Renal Function and 25-Hydroxyvitamin D Concentrations Predict Parathyroid Hormone Levels in Renal Transplant Patients," *Nephrol Dial Transplant*, 21:2621-2624 (2006).

Bouillon et al., "Influence of dialysate calcium concentration and vitamin D on serum parathyroid hormone during repetitive dialysis," *Kidney Int*, 7:422-432 (1975).

Brossard et al. "Influence of Glomerular Filtration Rate on Non-(1-84) Parathyroid Hormone (PTH) Detected by Intact PTH Assays," *Clinical Chemistry*, 46(5):697-703 (2000).

Brown et al., "The Vitamin D Prodrugs $1\alpha(OH)D_2$, $1\alpha(OH)D_3$ and BCI-210 Suppress PTH Secretion by Bovine Parathyroid Cells," *Nephrol Dial Transplant*, 21:644-650 (2006).

Brown et al., "Vitamin D Analogues for Secondary Hyperparathyroidism," Nephrol Dial Transplant, 17[Suppl. 10]:10-19 (2002).

Buccianti et al., "Effects of Calcifediol Treatment on the Progression of Renal Osteodystrophy during Continuous Ambulatory Peritoneal Dialysis," *Nephron*, 56:353-356 (1990).

Budavari (ed.), *Merck Index: an Encyclopedia of Chemicals, Drugs, and Biologicals*, 11th Edition, Merck & Co., 9927-9930 (1989).

Bulla et al., "Renal bone disorders in children: therapy with vitamin D3 or 1,25-dihydroxycholecalciferol," *Proc.Eur.Dial.Transplant.Assoc.*, 16: 644-648 (1979).

Chandra et al., "Cholecalciferol (vitamin D3) therapy and vitamin D insufficiency in patients with chronic kidney disease: a randomized controlled pilot study," *Endocr.Pract*, 14: 10-17 (2008).

Claris-Appiani et al., "Phosphate-Induced PTH Stimulation and Calcitriol Treatment in Children with Early Chronic Renal Insufficiency," *J. Bone Miner. Met.*, 12:S91-S97 (1994).

Coburn et al., "Doxercalciferol Safely Suppresses PTH Levels in Patients with Secondary Hyperparathyroidism Associated with Chronic Kidney Disease Stages 3 and 4," *Am. J. Kidney Dis.*, 43(5):877-890 (2004).

Coburn, "An Update on Vitamin D as Related to Nephrology Practice: 2003," *Kidney International*, vol. 64, Supplement 87, pp. S125-S130 (2003).

Coburn, et al., "Use of Active Vitamin D Sterols in Patients with Chronic Kidney Disease, Stages 3 and 5," *Kidney International*, vol. 63, Supplement 85, pp. S49-S53 (2003).

Coen et al., "1,25(OH)2D3 and 25-OHD3 in the Treatment of Renal Osteodystrophy: Comparison of Combined Versus 1,25(OH)2D3 Administration Alone," *Miner. Electrolyte Metab.*, 9:19-27 (1983).

Coen et al., "25-hydroxycholecalciferol in the treatment of renal osteodystrophy in haemodialysed patients," *Int J Artificial Organs*, 2(6): 278-281 (1979).

Cohen-Solal et al., "Non-Aluminic Adynamic Bone Disease in Non-Dialyzed Uremic Patients: A New Type of Osteopathy Due to Overtreatment?" *Bone*, 13:1-5 (1992).

Collet et al. "Modified-Release Peroral Dosage Forms," Aulton (ed.), Pharmaceutics: The Science of Dosage Forms, Churchill Livingston, London, pp. 289-305 (2002).

Colodro et al., "Effect of 25-Hydroxy-Vitamin D3 on Intestinal Absorption of Calcium in Normal Man and Patients With Renal Failure," *Metabolism*, 27(6):745-753 (1978).

Cooke et al., "Vitamin D-Binding Protein (Gc-Globulin): Update 1995," *Endocrine Rev.*, 4:125-128 (1995).

Coyne et al., "Paricalcitol Capsule for the Treatment of Secondary Hyperparathyroidism in Stages 3 and 4 CKD," *American Journal of Kidney Diseases*, 47(2):263-276 (2006).

Daisley-Kydd et al., "Calcitriol in the Management of Secondary Hyperparathyroidism of Renal Failure," *Pharmacotherapy.*, 16:619-630 (1996).

Davies, M. et al. The Absorption and Metabolism of Vitamin D3 from Parenteral Injection Sites, Proceedings of the Workshop on Vitamin D, 4th, Vitam. D: Basic Res. Its Clin. Appl. (1979), abstract.

DB-Pharma, "Dedrogyl 15 Mg/10ML Calcifediol Oral Drops, Solution," Marketing Authorization No. 317 863.2 (2000).

DeLuca, "Treatment of renal osteodystrophy with 25-hydroxycholecalciferol," *Arch Intern Med*, 126(5):896-899 (1970).

Deroisy et al., "Comparison of the Short-Term Effects of Three Oral Calcium-Vitamin D Formulations and Placebo on Calcium Metabolism," *Curr. Ther. Res.*, 59:370-378 (1998).

DeVille et al., "Effect of Ergocalciferol Supplementation on Serum Parathyroid Hormone and Serum 25-Hydroxyvitamin D in Chronic Kidney Disease," *Nephrology*, 11:555-559 (2006).

*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).

*Dietary Supplement Fact Sheet: Vitamin D*, National Institutes of Health, Office of Dietary Supplements (last update: Aug. 5, 2005), retrieved from <URL: http:ods.od.nih.gov/factsheets/vitamind.asp> on Aug. 31, 2007.

*Disease and Vitamin D*, University of California Riverside, retrieved from Internet, <URL: <http://vitamind.ucr.edu/disease.html>> (last update: May 19, 1999).

Disintegration, chapter 701; Dissolution, chapter 711; Distilling Range, chapter 721; Drug Release, chapter 724; Electrophoresis, chapter 726; pp. 276-292, in: U.S. Pharmacopeia vol. 30.

Dogan et al., "Effect of depot oral cholecalciferol treatment on secondary hyperparathyroidism in stage 3 and stage 4 chronic kidney diseases patients," *Ren Fail.*, 30: 407-410 (2008).

Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).

Dusso et al, "Metabolic Clearance Rate and Production Rate of Calcitriol in Uremia," *Kidney Int.*, 35 860-864 (1989).

Dusso et al., "Extra-renal production of calcitriol in chronic renal failure," *Kidney Int.*, 34:368-375 (1988).

Dusso et al., "Extrarenal Production of Calcitrol in Normal and Uremic Humans*," *Journal of Clinical Endocrinology and Metabolism*, 72(1):157-164 (1991).

Eastwood et al., "Biochemical and histological effects of 1,25 dihydroxycholecalciferol (1,25-DHCC) in the osteomalacia of chronic renal failure," *J Urol Nephrol (Paris,)* 80(12): 984-985 (1974).

Eastwood et al., "The contrasting effects on bone histology of vitamin D and of calcium carbonate in the osteomalacia of chronic renal failure," *Clin. Sci. Molec. Med.*, 47:23-42 (1974).

Eastwood et al., "The Effect of 25-Hydroxy Vitamin D3 in the Osteomalacia of Chronic Renal Failure," *Clin. Sci. Molec. Med.*, 52:499-508 (1977).

Epps et al., "Vitamin D Metabolism: Implications for Treatment in Oncology," *Oncology News*, 4:42-44 (2009).

Fernandez et al., "Guidelines for Dosing of Intravenous Calcitriol in Dialysis Patients with Hyperparathyroidism," Nephrol. Dial. Transplant., 11:96-101 (1996).

Fliser et al., Fibroblast gowth factor 23 (FGF23) predicts progression of chronic kidney disease: the mild to moderate kidney disease (MMKD) study, J. Am. Soc. Nephrol., 18:2601-8 (2007).

Fournier et al., "$1\alpha$ Hydroxycholecalciferol and 25 Hydroxycholecalciferol in Renal Bone Disease" Proc Eur Dial Transplant Assoc 12:227-236 (1976).

Fournier et al., "Advances in Nephrology from the Necker Hospital" *Adv. Nephrol Necker Hosp.* 21:237-306 (1992).

Fournier et al., "Comparison of $1\alpha$-hydroxycholecalciferol and 25-hydroxycholecalciferol in the treatment of renal osteodystrophy: Greater effect of 25-hydroxycholecalciferol on bone mineralization" Kidney International 15:196-204 (1979).

Fournier et al., "Current Status of the Management of Renal Osteodystrophy" *Proceedings of the European Dialysis and Transplant Association* 15:547-568 (1978).

Fournier et al., "Importance of Vitamin D Repletion in Uraemia," *Nephrol Dial Transplant*, 14(4):819-823 (1999).

(56) References Cited

OTHER PUBLICATIONS

Fournier et al., "Low doses of calcitriol or calcium carbonate for the prevention of hyperparathyroidism in predialysis patients?" *Nephrol Dial Transplant* 11(7):1493-1495 (1996).
Fournier et al., "Present-Day Concepts in the Treatment of Chronic Renal Failure" *Contrib Nephrol*. 71:64-80 (1989).
Fournier et al., "Preventing Renal Bone Disease in Moderate Renal Failure with CaCO3 and 25(OH) Vitamin D3," *Kidney Int.*, 33:S178-S279 (1988).
Fournier et al., "Renal Osteodystrophy in Dialysis Patients: Diagnosis and Treatment," *Artificial Organs*, 22:530-557 (1998).
Fournier et al., "Renal Osteodystrophy: Pathophysiology and Treatment" *Hormone Res*. 20:44-58 (1984).
Fournier et al., "The Approach to the Treatment of Secondary Hyperparathyroidism in Early Renal Failure" *Am. J. Nephrol* 8:170-172 (1988).
Fournier et al., "Traitement vitaminique D et ostéodystrophies rénales: indications et modalitiés" Nephrologie 16(2):165-190 (1995) [journal in French].
Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).
Friedman et al. "The Role of Vitamin D in Mild to Moderate Chronic Kidney Disease," *Trends in Endocrinology & Metab*,. 13(5):189-194 (2002).
Fritsche et al., "Regulation of 25-Hydroxyvitamin $D_3$-1α-Hydroxylase and Production of 1 α,25-Dihydroxyvitamin $D_3$ by Human Dendritic Cells," *Blood*, 102(9):3314-3316 (2003).
Frohling et al., "Serum 25-hydroxyvitamin D in patients with chronic renal failure on long-term treatment with high doses of vitamin D2." *Nephron* 26: 116-120 (1980).
Frost et al., "Histomorphometric Changes in Trabecular Bone of Renal Failure Patients Treated with Calcifediol," *Metab. Bone Dis. & Rel. Res.*, 2:285-295 (1981).
Fukagawa et al., FGF23: its role in renal bone disease, Pediatr. Nephrol., 21:1802-6 (2006).
Fukagawa et al., With or without the kidney: the role of FGF23 in CKD, Nephrol. Dial. Transplant., 20:1295-8 (2005).
Gal-Moscovici et al. 2007. Journal of Bone and Mineral Res. 22:V91-V94.
Gallagher et al., "Comparison of the Histological Effect and Metabolism of 25-(OH)D and 1,25-(OH)2D in Rat Bone," p. 399-401, In: Norman,*Vitamin D: Basic Research and its Clinical Application: Proceedings of the Fourth Workshop on Vitamin D*, Berlin, West Germany, Feb. 1979.
Ghazali et al., "Is low plasma 25-(OH) vitamin D a major risk factor for hyperparathyroidism and Looser's zones independent of calcitriol?" *Kidney International* 55:2169-2177 (1999).
Gibson, ed., Product optimisation. *Pharmaceutical Preformulation and Formulation: A Practical Guide from Candidate Drug Selection to Commercial Dosage Form*, 295-8 (2004).
Granja et al., "Studies on the Opening of Dioxanone and Acetal Templates and Application to the Synthesis of 1α,25-Dihydroxyvitamin $D_2$ $^1$," *J. Org. Chem.*, 58:124-131 (1993).
Gómez-Alonso et al., "Vitamin D Status and Secondary Hyperparathyroidism: The Importance of 25-Hydroxyvitamin D Cut-Off Levels," *Kidney International*, 63(Supp. 85):S44-S48 (2003).
Haddad et al., "Acute Administration of 25-Hydroxycholecalciferol in Man," *J. Clin. Endocrinol. Metab.*, 42:284-289 (1976).
Haddad et al., "Human Serum Binding Capacity and Affinity for 25-Hydroxyergocalciferol and 25-Hydroxycholecalciferol," *J. Clin. Endocrinol. Metab.*, 43:86-91 (1976).
Haddad et al., "Natural and Synthetic Sources of Circulating 25-Hydroxyvitamin D in Man," *Nature*, 244:515-517 (1973).
Haddad, "Plasma Vitamin D-binding Protein (Gc-Globulin): Multiple Tasks," *J. Steroid Biochem. Molec. Biol.*, 53:579-582 (1995).
Haddad, "Seasonal Diminution of Vitamin D Stores in the United States: Can Darker Winters Lead to Lighter Bones?" *Trends Endocrinol. Metab.*, 7:209-212 (1996).
Haddad, "Traffic, Binding and Cellular Access of Vitamin D Sterols," *Bone and Mineral Res.*, Elsevier, 5:281-308 (1987).
Haddad, "Vitamin D—Solar Rays, The Milky Way, or Both?" *NEJM*, 326:1213-1215 (1992).
Haldimann et al., "Effect of an Oral Dose of 25-Hydroxyvitamin D3 on Its Blood Levels in Patients with the Nephrotic Syndrome," *J Clin Endocrinology and Metabolism*, 50(3): 470-474 (1980).
Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).
Hamida et al., "Hyperparathyroïdie secondaire álinsuffisance rénale" Annales d'Endocrinologie 55:147-158 (1994) [reference in French].
Hannula et al., "Constant, But Not Pulsed Calcitriol Suppresses Hemodialysis Patients' Antigen-Induced Lymphocyte Proliferation," *Nephron*, 86:139-144 (2000).
Hari et al., "Vitamin D insufficiency and effect of cholecalciferol in children with chronic kidney disease," *Pediatr.Nephrol*,. 25: 2483-2488 (2010).
Hay et al., "Vitamin D2 in Vertebrate Evolution," *Comp. Biochem. Physiol. B*, 56:375-380 (1977).
Hodson et al., "Treatment of childhood renal osteodystrophy with calcitriol or ergocalciferol," *Clin Nephrology*, 24(4): 192-200 (1985).
Holick, "Vitamin D Deficiency in CKD: Why Should We Care?" *Am. J. Kidney Dis.*, 45:1119-1121 (2005).
Holick, "Vitamin D Status: Measurement, Interpretation and Clinical Application," *Ann Epidemiol*, 19(2):73-78 (2009).
Hollis, "Circulating 25-Hydroxyvitamin D Levels Indicative of Vitamin D Sufficiency: Implications for Establishing a New Effective Dietary Intake Recommendation for Vitamin D," *J. Nutr.* 135: 317-322 (2005).
Horst et al., "A Sensitive Competitive Protein Binding Assay for Vitamin D in Plasma," *Steroids*, 37:581-592 (1981).
Horst et al., "Discrimination in the Metabolism of Orally Dosed Ergocalciferol and Cholecalciferol by the Pig, Rat and Chick," *Biochem. J.*, 204:185-189 (1982).
Horst et al., "Rat cytochrome P450C24 (CYP24) does not metabolize 1,25-dihydroxyvitamin D2 to calcitroic acid," *J. Cell Biochem.*, 88:282-285 (2003).
Hottelart et al., "Ostéodystrophie rénale (2): son traitement chez l'insuffisant rénal avant la dialyse" Nephrologie 21(6):275-282 (2000) [reference in French].
Houghton et al., "The Case Against Ergocalciferol (Vitamin D2) as a Vitamin Supplement," *Am. J. Clin. Nutr.*, 84:694-697 (2006).
Hunt, et al., "A Comparison of the Toxicity of Ergocalciferol and Cholecalciferol in Rhesus Monkeys (*Macaca mulatta*)," J. Nutrition, 102:975-986 (1972).
Hussar, "New Drugs of 1999," *J. Am. Pharmacist. Assoc*. 40(2):181-229 (2000).
Ibrahim et al., Serum fibroblast growth factor-23 levels in chronic haemodialysis patients, Int. Urol. Nephrol., 41:163-9 (2009).
Inoue et al., Role of the vitamin D receptor in FGF23 action on phosphate metabolism, Biochem. J., 399:325-31 (2005).
International Preliminary Report on Patentability for corresponding International Application No. PCT/US09/39355, dated Oct. 5, 2010.
International Search Report and Written Opinion for corresponding International Application No. PCT/US09/39355, dated Jun. 17, 2009.
International Search Report for Application No. PCT/US2007/061521, dated Jul. 17, 2007.
International Search Report of counterpart PCT/US2008/061579 dated Aug. 21, 2008 (5 pages).
Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.*, 55:1019-1027 (1999).
Japanese Office Action for Application No. 2008-553520, dated Jul. 24, 2013.
Jara et al., "Effect of Calcitriol Treatment and Withdrawal on Hyperparathyroidism in Haemodialysis Patients with Hypocalcaemia," *Nephrol. Dial. Transplant.*, 16:1009-1016 (2001).

(56) References Cited

OTHER PUBLICATIONS

Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant*, 23:3670-3676 (2008).

Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).

Jean et al., "Monthly cholecalciferol administration in heamodialysis patients: a simple and efficient strategy for vitamin D supplementation" *Nephrol. Dial. Transplant* 24(12):3799-3805 (2009).

Jones, "Pharmacokinetics of vitamin D toxicity," *Am. J. Clin. Nutr.* 88(suppl): 582S-6S (2008).

Jones., "Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin D3," *Seminars in Dialysis*, 20(4):316-324 (2007).

Joy et al., Outcomes of secondary hyperparathyroidism in chronic kidney disease and the direct costs of treatment, *J. Managed Care Pharm.*, 13:397-411 (2007).

K/DOQI clinical practice guidelines for bone metabolism and disease in chronic kidney disease, *Am. J. Kidney Dis.*, 42:S1-201 (2003).

Kajihara et al., "Novel Method to Control Release of Lipophilic Drugs with High Potency from Silicone," *Chem. Pharm. Bull.*, 51:11-14 (2003).

Kalantar-Zadeh et al., "Clinical Outcomes with Active versus Nutritional Vitamin D Compounds in Chronic Kidney Disease" *Clin J Am Soc Nephrol.* 4(9):1529-1539 (2009).

Kanis et al., "Rate of Reversal of Hypercalcaemia and Hypercalciuria Induced by Vitamin D and Its 1-alpha-Hydroxylated Derivatives," *BMJ*, 1:78-81 (1977).

Kazama et al., Role of circulating fibroblast growth factor 23 in the development of secondary hyperparathyroidism, Ther. Apher. Dial., 9:328-30 (2005).

Khachane et al., "Novel Sustained Release Drug Delivery System: Review," *IJPRD*, 3(12):1-14 (2012).

Kim, *Advanced Pharmaceutics: Physicochemical Principles*, pp. 362-392, Boca Raton, Fla: CRC Press (2004).

Kinoshita et al., "1,25-Dihydroxyvitamin D Suppresses Circulating Levels of Parathyroid Hormone in a Patient with Primary Hyperparathyroidism and Coexistent Sarcoidosis," *J. Clin. Endo. & Metabol.*, 90(12):6727-6731 (2005).

Kleinman et al., "Effects of Calcifediol on Calcified Tissue in Uremia," *Arch Intern Med*, 138: 864-865 (1978).

Kobayashi et al., "2β-(3-Hydroxyproxy)-α,25-Dihydroxyvitamin $D_3$ (ED-71), Preventive and Therapeutic Effects on Bone Mineral Loss in Ovariectomized Rats," *Bioorganic & Medicinal Chemistry Letters*, 3(9):1815-1819 (1993).

Kobayashi et al., "Variation of 25-Hydroxyvitamin D3 and 25-Hydroxyvitamin D2 Levels in Human Plasma Obtained from 758 Japanese Healthy Subjects," *J. Nutr. Sci. Vitaminol* (Tokyo), 29(3):271-281 (1983). Abstract Only.

Kooienga et al., "The effect of combined calcium and vitamin D3 supplementation on serum intact parathyroid hormone in moderate CKD," *Am.J.Kidney Dis,.* 53: 408-416 (2009).

Koshikawa, et al., "Clinical Effect of Intravenous Calcitriol Administration on Secondary Hyperparathyroidism," Nephron; 90:413-423 (2002).

Kuro-O, Klotho in chronic kidney disease—what's new?, Nephrol. Dial. Transplant., 4 pp. (2009).

LaClair et al., "Prevalence of Calcidiol Deficiency in CKD: A Cross-Sectional Study Across Latitudes in the United States," *Am. J. Kidney Dis.*, 45:1026-1033 (2005).

Lafage et al., "Ketodiet, Physiological Calcium Intake and Native Vitamin D Improve Renal Osteodystrophy," *Kidney Int.*, 42:1217-1225 (1992).

Lambert et al., "Evidence for Extranrenal Production of 1-alpha,25-Dihydroxyvitamin D in Man," *J. Clin. Invest.*, 69:722-725 (1982).

Lambrey et al., "24, 25 Dihydroxycalciferol: Assay in Non-Anephric Patients on Chronic Haemodialysis and Assessment of it's Possible Pathophysiological Role in Renal Osteodystrophy" *Proc Eur Dial Transplant Assoc.* 17:548-556 (1980).

Lambrey, "Possible Link Between Changes in Plasma 24,25-Dihydroxyvitamin D and Healing of Bone Resorption in Dialysis Osteodrstrophy" *Metab. Bone Dis. & Rel. Res.* 4:25-30 (1982).

Langman et al., "25-Hydroxyvitamin D3 (Calcifediol) Therapy of Juvenile Renal Osteodystrophy: Beneficial Effect on Linear Growth Velocity," *J. Pediatrics*, 100:815-820 (1982).

Larrosa M. et al., Long-Term Treatment of Hypovitaminosis D. Calcidol or Cholecalciferol? *Annals of the Rheumatic Diseases*, vol. 64, No. Suppl. 3, Jul. 2005, p. 366.

Lau et al., "Vitamin D Therapy of Osteoporosis: Plain Vitamin D Therapy Versus Active Vitamin D Analog (D-Hormone) Therapy," *Calcif. Tissue Int.*, 65:295-306 (1999).

Lehmann et al., "Coating of Tablets and Small Particles with Acrylic Resins by Fluid Bed Technology," *Int. J. Pharm. Tech. & Prod. Mfr.*, 2:31-43 (1981).

Letteri et al., "Effects of 25-Hydroxycholecalciferol on Calcium Metabolism in Chronic Renal Failure" Adv. Exp. Med. Biol. 81:591-601 (1977).

Lips et al., "A Global Study of Vitamin D Status and Parathyroid Function in Postmenopausal Women with Osteoporosis: Baseline Data from the Multiple Outcomes of Raloxifene Evaluation Clinical Trial," *The Jour. of Clin. Endo. & Meta.*, 86(3):1212-1221 (2001).

Lomonte et al., "Are Low Plasma Levels of 25-(OH) Vitamin D a Major Risk Factor for Hyperparathyroidism Independent of Calcitriol in Renal Transplant Patients?" *J. Nephrol.*, 18:96-101 (2005).

Lund et al., "Serum 1,25-Dihydroxycholecalciferol in Anephric. Haemodialyzed and Kidney-transplanted Patients," *Nephron*, 25:30-33 (1980).

Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).

Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.*, 11:61-64 (1997).

Martin et al., "19-Nor-1-α-25 Dihydroxyvitamin $D_2$ (Paricalcitol) Safely and Effectively Reduces the Levels of Intact Parathyroid Hormone in Patients on Hemodialysis," *J. Am. Soc. Nephrol.*, 9:1427-1432 (1998).

Matsushita et al., "Clinical effects of 25-hydroxycholecalciferol in patients with chronic renal failure," *J Nutr Sci Vitaminol*, 23:257-261 (1977).

Mazouz et al., "Risk factors of renal failure progression two years prior to dialysisis" Clinical Nephrology 51(6):355-366 (1999).

Mazur, "Effects of 25-OHD3 on Renal Function in Pediatric Patients with Chronic Renal Failure," *Mineral Electrolyte Metab.* 10:351-358 (1984).

Memmos et al., "Response of uremic osteoid to vitamin D," Kidney Int, 21(Suppl. 11): S50-S54 (1982).

Menon et al., "Vitamin D insufficiency and hyperparathyroidism in children with chronic kidney disease," Pedaitr Nephrol, 23:1831-1836 (2008).

Messa et al., "Direct in Vivo Assessment of Parathyroid Hormone-Calcium Relationship Curve in Renal Patients," *Kidney Int.*, 46:1713-1720 (1994).

Minutes of US FDA E&M Advisory Committee Meeting of Oct. 4, 1979 for Calderol® calcifediol capsules.

Moe et al., "A randomized trial of cholecalciferol versus doxercalciferol for lowering parathyroid hormone in chronic kidney disease," *Clin.J.Am.Soc.Nephrol.* 5: 299-306 (2010).

Moe et al., "Safety and Efficacy of Pulse and Daily Calcitriol in Patients on CAPD: A Randomized Trial," *Nephrol. Dial. Transplant.*, 13:1234-1241 (1998).

Morris, "Cats Discriminate Between Cholecalciferol and Ergocalciferol," *J. Anim. Physiol. a. Anim. Nutr.*, 86:229-238 (2002).

(56) References Cited

OTHER PUBLICATIONS

Morris, "Vitamin D: A Hormone for All Seasons—How Much is Enough?" *Clin. Biochem. Rev.*, 26:21-32 (2005).
Muindi et al., "Phamacokinetics of Liquid Calcitriol Formulation in Advanced Solid Tumor Patients: Comparison with Caplet Formulation," *Cancer. Chemother. Pharmacol.*, 56:492-496 (2005).
Naik et al., "Effects of Vitamin D Metabolites and Analogues on Renal Function," *Nephron*, 28:17-25 (1981).
Nakanishi et al., "The Roles of Vitamin D in Secondary Hyperparathyroidism," [journal in Japanese] 52:1107-1112 (2004).
Norman et al. (eds.), *Vitamin D—Gene Regulation, Structure-Function Analysis and Clinical Application: Proceedings of the Eighth Workshop on Vitamin d Paris, France*, pp. 765-766, New York: Walter De Gruyter Inc. (1991).
Notice of allowance dated Jul. 10, 2012, in EPO application 08746908.6.
Oksa et al., "Effects of long-term cholecalciferol supplementation on mineral metabolism and calciotropic hormones in chronic kidney disease," *Kidney Blood Press Res.*, 31: 322-329 (2008).
Parfitt et al., "Calcitriol But No Other Metabolite of Vitamin D is Essential for Normal Bone Growth and Development in the Rat," *J. Clin. Invest.*, 73:576-586 (1984).
Parise et al., CYP24, the enzyme that catabolizes the antiproliferative agent vitamin D, is increased in lung cancer, Int. J. Cancer, 119:1819-28 (2006).
Patel et al., "Glomerular Filtration Rate is a Major Determinant of the Relationship Between 25-Hydroxyvitamin D and Parathyroid Hormone," *Calcif. Tissue Int.*, 80:221-226 (2007).
Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).
Perrie, Pharmaceutics: Drug Delivery and Targeting, Second Edition, Chapter 1 (2012).
Petkovich et al., "CYP24A1 and Kidney Disease," *Current Opin. in Nephrology and Hypertension*, 20:337-344 (2011).
Phadnis et al., "Direct, Rapid Effects of 25-Hydroxyvitamin D3 on Isolated Intestinal Cells," *J. Cell. Biochem.*, 90:287-293 (2003).
Posner et al., "Vitamin D Analogues Targeting CYP24 in Chronic Kidney Disease," *J. Steroid Biochem and Mol. Biol.*, 121:13-19 (2010).
Pourgholami et al., "1, 25-Dihydroxyvitamin D3 Dissolved in Lipiodol Produces a Sustained Antiproliferative Effect in the Human Hepatoblastoma Cell Line HepG2," *Anticancer Res.*, 20:723-728 (2000).
Pourgholami et al., "In Vitro Antiproliferative Activity of a Medium-Chain Triglyceride Solution of 1, 25-Dihydroxyvitamin $D_3$ in HepG2 Cells," *Anticancer Res.*, 20:4257-4260 (2000).
Prescribing Information for Calderol® calcifediol capsules (1988).
Prescribing Information for Hectorol® (doxercalciferol capsules), Genzyme (2011).
Rambeck et al., "Biological Activity of 1α,25-Dihydroxyergocalciferol in Rachitic Chicks and in Rats," *IZVIAK*, 54(2/3):135-139 (1984).
Rapuri, P.B. et al., "Effect of Vitamins D2 and D3 Supplement Use on Serum 25-OHD Concentration in Elderly Women in Summer and Winter," Calcified Tissue International, 74(2):150-156 (2004).
Recker et al., "The Efficacy of Calcifediol in Renal Osteodystrophy," *Arch. Intern. Med.*, 138:857-863 (1978).
Reddy et al., *Abstracts Sixth Annual Scientific Meeting of the American Society for Bone and Mineral Research*, 36:524 (1984).
Reichel et al., "Calcium Metabolism in Early Chronic Renal Failure: Implications for the Pathogenesis of Hyperparathyroidism," *Nephrol. Dial. Transplant.*, 6:162-169 (1991).
Reichel et al., "Intermittent Versus Continuous Administration of 1,25-dihydroxyvitamin D3 in experimental renal hyperparathyroidism," *Kidney Int.*, 44:1259-1265 (1993).
Reichel, "Current treatment options in secondary renal hyperparathyroidism," *Nephrol Dial Transplant* 21:23-28 (2006).

Ritter et al., "25-Hydroxyvitamin D3 suppresses PTH synthesis and secretion by bovine parathyroid cells," *Kidney Int.*, 70:654-659 (2006).
Rix et al., "Effect of 18 Months of Treatment with Alfacalcidol on Bone in Patients with Mild to Moderate Chronic Renal Failure," *Nephrol Dial Transplant*, 19:870-876 (2004).
Rucker et al., "Vitamin D insufficiency and treatment with oral vitamin D3 in northern-dwelling patients with chronic kidney disease," *J.Nephrol.* 22: 75-82 (2009).
Russell et al., "Therapeutic Effects of 25-Hydroxyvitamin D3 on Renal Osteodystrophy," *Mineral Electrolyte Metab.*, 1:129-138 (1978).
Rutherford et al., "Effect of 25-Hydroxycholecalciferol on Calcium Absorption in Chronic Renal Disease," Kidney International, 8:320-324 (1975).
Saab et al., "Prevalence of Vitamin D Deficiency and the Safety and Effectiveness of Monthly Ergocalciferol in Hemodialysis Patients," *Nephron Clin. Pract.*, 105:c132-c138 (2007).
Sanchez, "Prevention and Treatment of Renal Osteodystrophy in Children With Chronic Renal Insufficiency and End-Stage Renal Disease," *Seminars in Nephrology*, 21:441-450 (2001).
Schmidt, "Measurement of 25-Hydroxyvitamin D Revisited," *Clinical Chemistry*, 52(12):2304-2305 (2006).
Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).
Sebert et al., "Effets a Long Terme D'Une Association De 25-Hydroxycholécalciférol et de 1-Alpha-Hydroxycholécalciférol Sur L'Ostéodystrophie Des Hémodialysés Chroniques" Rev. Rhum Mal Osteoartic 48(7-9):535-541 (1981).
Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).
Sekkarie, "The Impact of Over-the-counter Vitamin D Supplementals on Vitamin D and Parathyroid Hormone Levels in Chronic Kidney Disease," *Clin. Nephrology*, 65:91-96 (2006).
Shah et al., "Prevalence and correction of 25(OH) vitamin D deficiency in peritoneal dialysis patients," *Peritoneal Dialysis Int.*, 25:362-366 ( 2005).
Shi et al., "Preparation of Chitosan/Ethylcellulose Complex Microcapsule and its Application in Controlled Release of Vitamin $D_2$," *Biomaterials*, 23:4469-4473 (2002).
Singh et al., "C-3 Epimers Can Account for a Significant Proportion of Total Circulating 25-Hydroxyvitamin D in Infants, Complicating Accurate Measurement and interpretation of Vitamin D Status," *J. Clin. Endo. & Metabol.*, 91(8):3055-3061 (2006).
Sjoden, et al., "1α-Hydroxyvitamin D2 is Less Toxic than 1α-Hydroxyvitamin D3 in the Rat," Society for Experimental Biology and Medicine, 179: 432-436 (1985).
Skelly et al., In vitro and in vivo testing an correlation for oral controlled/modified-release dosage forms. *Pharm. Res.*, 7(9):975-82 (1990).
Slatopolsky et al., "Differential Effects of 19-nor-1,25-$(OH)_2D_2$ and 1α-Hydroxyvitamin $D_2$ on Calcium and Phosphorus in Normal and Uremic Rats," *Kidney International*, 62:1277-1284 (2002).
Somerville et al., "Resistance to Parathyroid Hormone in Renal Failure: Role of Vitamin D Metabolites," *Kidney Int.*, 14:245-254 (1978).
Sommerfeldt et al., "Metabolism of Orally Administered [3H]Ergocalciferol and [3H]Cholecalciferol by Dairy Calves," *J. Nutr.*, 113:2595-2600 (1983).
Sosa et al., "The Effect of 25-dihydroxyvitamin D on the Bone Mineral Metabolism of Elderly Women with Hip Fracture," *Rheumatology*, 39:1263-1268 (2000).
Stamp et al., "Comparison of Oral 25-Hydroxycholecalciferol, Vitamin D, and Ultraviolet Light as Determinants of Circulating 25-Hydroxyvitamin D," *The Lancet*, 1341-1343 (Jun. 25, 1977).
Stamp, "Intestinal Absorption of 25-hydroxycholecalciferol," *The Lancet*, 121-123 (1974).

(56) References Cited

OTHER PUBLICATIONS

Stein et al., "An Update on the Therapeutic Potential of Vitamin D Analogues," *Expert Opin. Investig. Drugs*, 12:825-840 (2003).
Stubbs et al., "Cholecalciferol supplementation alters calcitriol-responsive monocyte proteins and decreases inflammatory cytokines in ESRD," *J.Am.Soc.Nephrol.*, 21: 353-361 (2010).
Stumpf, "The Dose Makes the Medicine," *Drug Discovery Today*, 11:550-555 (2006).
Supplementary European Search Report for Application No. 09729007.6, dated Apr. 18, 2011.
Szycher, *Szycher's Dictionary of Biomaterials and Medical Devices*, pp. 20, 48, 127, Lancaster, Penn: Technomic Publishing Co., Inc. (1992).
Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).
Taylor et al., "Interrelationship of Serum 25-Hydroxyvitamin D3 and 1,25-Dihydroxyvitamin D in Juvenile Renal Osteodystrophy after Therapy with 25-Hydroxyvitamin D3," *Metab. Bone Dis. & Rel. Res.*, 4:255-261 (1982).
Taylor et al., "The absence of 24,25-dihydroxycholecalciferol in anephric patients," *Clin.Sci.Mol.Med.Suppl.*, 55: 541-547 (1978).
Taylor, CM, 24,25-Dihydroxyvitamin D in Human Serum. In: Vitamin D. Basic Research and Clinical Applications, pp. 197-203. Walter de Gruyter, New York (1979).
Tebben et al., Elevated fibroblast growth factor 23 in women with malignant ovarian tumors, *Mayo Clin. Proc.*, 80:745-51 (2005).
Teitelbaum et al., "Calcifediol in Chronic Renal Insufficiency" *JAMA* 235(2):164-167 (1976).
Teitelbaum et al., "Tetracycline fluorescence in uremic and primary hyperparathyroid bone," *Kidney Int.*, 12:366-372 (1977).
Thomas et al., "Hypovitaminosis D in Medical Inpatients," *NEJM*, 338:777-783 (1998).
Thombre, "Assessment of the feasibility of oral controlled release in an exploratory development setting," *Drug Discovery Today*, 10(17): 1159-1166 (2005).
Tokmak et al., "High-dose cholecalciferol to correct vitamin D deficiency in haemodialysis patients," *Nephrol.Dial.Transplant.*, 23: 4016-4020 (2008).
Trakarnvanich et al., "Effect of high dose ergocalciferol in chronic kidney disease patients with 25-hydroxyvitamin D deficiency," *J.Med.Assoc.Thai.* 93: 885-891 (2010).
Tuohimaa et al., "Both High and Low Levels of Blood Vitamin D are Associated with a Higher Prostate Cancer Risk: A Longitudinal, Nested Case-Control Study in the Nordic Countries," Int. J. Cancer, 108(1):104-108 (2004).
US FDA Clinical Review and Evaluation of NDA for Calderol® calcifediol capsules (believed to be available circa 1983).
US FDA Summary of Basis of Approval for Calderol® calcifediol capsules (believed to be available circa 1980).
Van Weelden et al., "Apoptotic Regression of MCF-7 Xenografts in Nude Mice Treated with the Vitamin $D_3$ Analog, EB1089," *Endocrinology*, 139:2102-2110 (1998).
Verberckmoes et al., "Osteodystrophy of Dialysed Patients Treated with Vitamin D," *Proc Eur Dial Transplant Assoc.*, 10(0): 217-226 (1973).
Vieth, "Vitamin D Supplementation, 25-Hydroxyvitamin D Concentrations, and Safety," Am. J. Clin. Nutr., 69:842-856 (1999).
Vieth, "What is the optimal vitamin D status for health?" *Prog. Biophys. Mol. Biol.*, 92:26-32 (2006).
Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).
Witmer et al., "Effects of 25-hydroxycholecalciferol on bone lesions of children with terminal renal failure" *Kidney International* 10:395-408 (1976).
Wootton, "Improving the Measurement of 25-Hydroxyvitamin D," *Clin Biochem Rev*, 26:33-36 (2005).
Written Opinion for Application No. PCT/US2007/061521, dated Jul. 17, 2007.
Written Opinion for Application No. PCT/US2008/061579, dated Aug. 21, 2008.
Yanoff et al., "The Prevalence of Hypovitaminosis D and Secondary Hyperparathyroidism in Obese Black Americans," *Clin. Endocrinol. (Oxf)*, 64(5):523-529 (2006).
Zemplar® (paricalcitol) Capsules, Abbott (2011).
Zerwekh et al., "Extra-Renal Production of 24,25-Dihydroxyvitamin D in Chronic Renal Failure During 25 Hydroxyvitamin D3 Therapy," *Kidney Int.*, 23:401-406 (1983).
Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).
Zucchelli et al., "Therapeutic effects of 25-hydroxycholecalciferol and sodium etidronate on renal osteodystrophy," *Mineral. Electrolyte Metab.* 7: 86-96 (1982).
AlfaD3® 0.25, 0.5 or 1 microgram Capsules (Alfacalcidol, Package Leaflet, Apr. 2010).
Alfarol® Capsules 31 µg (Package Leaflet, Mar. 2011).
Ashford, Chapter 20: Bioavailability—physicochemical and dosage form factors, pp. 314-333 in: Aulton et al. (eds.), Aulton's Pharmaceutics. The Design and Manufacture of Medicines, Fourth Edition, Elsevier Publishing (2013).
Hectorol® (doxercalciferol) Capsules (Label, FDA, 2010).
Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).
Sitrin et al., Comparison of vitamin D and 25-hydroxyvitamin D absorption in the rat, Am. J. Physiol., 242(4):G326-32 (1982).
Zemplar® (paricalcitol) Capsules, Final Agreed Upon Label (FDA, May 5, 2009).

\* cited by examiner

* p< 0.05 compared to Normal diet group
** p< 0.05 compared to Vehicle group
*** p<0.05 compared to Calcitriol group

* p< 0.05 compared to Normal diet group
** p< 0.05 compared to Vehicle group
*** p<0.05 compared to Calcitriol group

METHODS USEFUL FOR VITAMIN D DEFICIENCY AND RELATED DISORDERS

CROSS-REFERENCE TO RELATED APPLICATIONS

This is a continuation of U.S. patent application Ser. No. 14/607,725, filed Jan. 28, 2015 (to be issued as U.S. Pat. No. 9,500,661), which is a division of U.S. patent application Ser. No. 12/935,139, filed Nov. 12, 2010 (now U.S. Pat. No. 8,962,239), which is the U.S. national phase of International Application No. PCT/US2009/039355, filed Apr. 2, 2009, which claims the benefit of U.S. Provisional Patent Application Ser. No. 61/041,898, filed Apr. 2, 2008, and 61/161,292, filed Mar. 18, 2009, the entire disclosures of which are hereby incorporated herein by reference.

BACKGROUND

Field of the Disclosure

The disclosure relates generally to methods for diagnosing and treating diseases and disorders, and related compositions and kits useful therefor. More particularly, the disclosure relates to methods for diagnosing and treating catabolism-related vitamin D deficiency and susceptibility thereto, related compositions and kits, and methods for preventing and treating related disorders.

Brief Description of Related Technology

Humans acquire vitamin D from dietary sources and from the UV light-dependent conversion of 7-dehydroxcholesterol to vitamin $D_3$. Vitamin $D_3$ (or cholecalciferol) and vitamin $D_2$ (or ergocalciferol) are collectively referred to as "vitamin D" and are fat-soluble precursors to the active vitamin D hormones. Metabolism of vitamin $D_3$ and vitamin $D_2$ occurs primarily in the liver to produce 25-hydroxyvitamin $D_3$ and 25-hydroxyvitamin $D_2$, respectively (collectively referred to herein as "25-hydroxyvitamin D"), which are prohormones of the respective active vitamin D hormones. Further metabolic activation of these vitamin D prohormones occurs mainly in the kidneys by a cytochrome P450 enzyme, CYP27B. CYP27B is also expressed in many extra-renal vitamin D target tissues and can effect local activation of 25-hydroxyvitamin D to produce autocrine and/or paracrine hormonal responses. Specifically, 25-hydroxyvitamin $D_3$ is metabolized to the active hormone 1,25-dihydroxyvitamin $D_3$ (or calcitriol) and 25-hydroxyvitamin $D_2$ is metabolized to the active hormone 1,25-dihydroxyvitamin $D_2$ (collectively referred to herein as "1,25-dihydroxyvitamin D").

The vitamin D hormones regulate a variety of cellular processes via interactions with vitamin D receptors (VDR). In particular, the vitamin D hormones regulate blood calcium levels by controlling the absorption of dietary calcium by the small intestine and the reabsorption of calcium by the kidneys. Excessive hormone levels can lead to abnormally elevated urine calcium (hypercalciuria), blood calcium (hypercalcemia) and blood phosphorus (hyperphosphatemia). Vitamin D deficiency, on the other hand, is associated with secondary hyperparathyroidism, parathyroid gland hyperplasia, hypocalcemia, chronic kidney disease (CKD), and metabolic bone diseases such as osteitis fibrosa cystica, osteomalacia, rickets, osteoporosis, and extraskeletal calcification. Vitamin D hormone has been reported to have many diverse "non-classical" biologic effects beyond its "classical" effects on the parathyroid hormone system. Such effects have been reported in connection with cellular proliferation, the immune system and the cardiovascular system, including the renin-angiotensin system, blood pressure, cellular growth and differentiation, antifibrosis, red blood cell formation, hair growth, and muscular function.

Catabolism of vitamin D prohormones, hormones, and analogs is accomplished through the action of cytochrome P450 enzymes. The cytochrome P450 enzyme CYP24 catalyzes the first step in the catabolism of various vitamin D compounds. In particular, for example, CYP24 carries out the conversion of 25-hydroxyvitamin $D_3$ to 24,25-dihydroxyvitamin $D_3$ and the conversion of 1,25-dihydroxyvitamin $D_3$ (calcitriol) to 1,24,25-trihydroxyvitamin $D_3$ eventually giving rise to calcitroic acid. CYP24 can also hydroxylate at the 23 position, resulting in the production of the terminal metabolite 1,25-dihydroxyvitamin $D_3$-26,23-lactone. Further processing by Phase II catabolic enzymes ultimately leads to clearance of vitamin D compounds from the body.

SUMMARY

One aspect of the disclosure herein is a method of diagnosing susceptibility for catabolism-related vitamin D deficiency in a patient, including measuring a patient's level of CYP24 expression and/or activity, or a proxy indicative thereof, for example by obtaining a tissue, blood, or cell sample from a patient and assaying the sample for CYP24 expression and/or activity, or a proxy indicative thereof, wherein abnormally elevated CYP24 expression and/or activity indicates a susceptibility for catabolism-related vitamin D deficiency. In one embodiment, the patient is vitamin D replete, and the method further includes inhibiting and/or preventing vitamin D deficiency by administering a CYP24 inhibitor to the patient in response to abnormally elevated CYP24 expression and/or activity. In another embodiment, the patient is vitamin D deficient, and the method further includes treating the vitamin D deficiency by administering a CYP24 inhibitor to the patient in response to abnormally elevated CYP24 expression and/or activity.

Another aspect of the disclosure herein is a method of diagnosing susceptibility for catabolism-related vitamin D deficiency in a patient, including measuring a patient's level of FGF23, for example by obtaining a tissue, blood, or cell sample from a patient and assaying the sample for FGF23 concentration, wherein abnormally elevated FGF23 concentration indicates a susceptibility for catabolism-related vitamin D deficiency. The method can further include any one of the treatment or prevention methods described herein.

Another aspect of the disclosure herein is a method of diagnosing and treating a patient, including measuring a patient's CYP24 expression and/or activity, or a proxy indicative thereof, and administering a CYP24 inhibitor to the patient in response to abnormally elevated CYP24 expression and/or activity. The method can further include obtaining a tissue, blood, or cell sample from the patient and assaying the sample for CYP24 expression and/or activity, or a proxy indicative thereof.

Preferably at the time of the measurement of CYP24 expression and/or activity, or proxy indicative thereof, the patient is not undergoing active vitamin D therapy.

Preferably, the patient is one who does not have cancer.

The method can further include measuring the patient's 25-hydroxyvitamin D levels and treating vitamin D deficiency by administering the CYP24 inhibitor to a vitamin D deficient patient.

The method can further include administering to the patient one or more of vitamin D prehormones, prohormones, and analogs of any of the foregoing, preferably a compound selected from cholecalciferol, ergocalciferol, 25-hydroxyvitamin $D_2$, 25-hydroxyvitamin $D_3$, and combinations thereof. For example the therapy can include administration of 25-hydroxyvitamin $D_3$. Preferably the therapy includes administration of a therapeutically effective amount of 25-hydroxyvitamin $D_3$ to restore the patient's 25-hydroxyvitamin D levels to at least 30 ng/mL.

The method can further include measuring the patient's 25-hydroxyvitamin D levels and inhibiting and/or preventing vitamin D deficiency by administering the CYP24 inhibitor to a vitamin D replete patient.

In one type of embodiment, the patient has Chronic Kidney Disease, for example selected from Stage 1 and Stage 2, or selected from Stage 3 and Stage 4.

In one type of embodiment, the patient has hyperparathyroidism. For example, the patient's PTH level is above the target range for the patient's Stage of CKD.

In one type of embodiment, the patient has a deficiency in 1,25-dihydroxyvitamin $D_3$.

The method can further include avoiding active vitamin D therapy or reducing the level of or omitting active vitamin D therapy if the patient is undergoing active vitamin D therapy.

The method can further include administering 25-hydroxyvitamin D to the patient in an amount sufficient to increase 1,25-dihydroxyvitamin D levels.

In one embodiment, the CYP24 inhibitor is also a vitamin D receptor agonist.

The method can include measuring the level of FGF23 in the patient as a proxy for the level of CYP24 expression and/or activity, wherein a level of FGF23 greater than the upper value of the normal range indicates abnormally elevated CYP24 expression. For example, a level of FGF23 at least two times, at least four times, at least 10 times, or at least 40 times greater than the upper value of the normal range indicates abnormally elevated CYP24 expression.

The method can include measuring the concentration of one or more catabolic byproducts of CYP24 in serum or another bodily fluid as a proxy for CYP24 activity.

The method can further include measuring the concentration of one or more precursors to the one or more catabolic byproducts of CYP24 in serum or another bodily fluid and calculating a ratio of concentrations of one or more catabolic byproducts of CYP24 to serum concentrations of one or more corresponding precursors as a proxy for CYP24 activity.

In one embodiment, the catabolic byproducts of CYP24 include one or both of 24,25-dihydroxyvitamin D and 1,24,25-trihydroxyvitamin D.

In one embodiment, the measuring of CYP24 activity includes measuring one or more ratios selected from the group consisting of 24,25-dihydroxyvitamin D to 25-hydroxyvitamin D and 1,24,25-trihydroxyvitamin D to 1,25-dihydroxyvitamin D.

In one embodiment, the catabolic byproducts of CYP24 include the 24-hydroxylated and/or 23-hydroxylated catabolic byproducts of one or more members selected from the group consisting of paricalcitol, doxercalciferol, 22-oxacalcitriol, dihydrotachysterol, and 26,26,26,27,27,27-hexafluorocalcitriol (falecalcitriol).

In one embodiment, the measuring of CYP24 expression and/or activity, or proxy indicative thereof follows acute or chronic administration of a CYP24 substrate. In this embodiment, preferably the CYP24 substrate is not a dual-action inhibitor and VDR agonist, as described below.

In one embodiment, one or more measurements comprise serum concentrations.

In one embodiment, the measuring of CYP24 expression includes measuring CYP24 mRNA in tissues, plasma, or cells.

In one embodiment, the measuring of CYP24 expression includes measuring CYP24 protein in tissues, plasma, or cells.

In one embodiment, the measuring of CYP24 activity includes measuring CYP24 enzymatic activity in tissues, plasma, or cells.

In one embodiment, the tissues or cells are selected from the group consisting of kidney tissue, liver tissue, parathyroid gland tissue, peripheral blood mononuclear cells, and buccal cells.

In one embodiment, the abnormally elevated CYP24 expression and/or activity is at least 2-fold, at least 3-fold, at least 4-fold, at least 10-fold, or at least 100-fold increased over normal CYP24 expression and/or activity.

Another aspect of the disclosure includes a kit, including an assay for measuring the levels of one or more CYP24 catabolic byproducts, and instructions for practicing a method described herein. The kit can further include an assay for measuring the levels of one or more corresponding precursors.

Another aspect of the disclosure includes a kit including an assay for measuring the level of CYP24 protein, and instructions for practicing a method described herein. The assay can include an immobilized anti-CYP24 antibody, and a labeled anti-CYP24 antibody.

Another aspect of the disclosure includes a pharmaceutical formulation for treating or preventing vitamin D deficiency including an effective amount of a CYP24 inhibitor. The formulation can further include an effective amount of 25-hydroxyvitamin $D_3$.

Another aspect of the disclosure includes a pharmaceutical formulation for treating or preventing hyperparathyroidism including an effective amount of a CYP24 inhibitor. The formulation can further include an effective amount of 25-hydroxyvitamin $D_3$. The pharmaceutical formulation can be for treating hyperparathyroidism secondary to Chronic Kidney Disease, for example Stage 3 or Stage 4 CKD.

Another aspect of the disclosure includes a CYP24 inhibitor for use in treating or preventing vitamin D deficiency.

Another aspect of the disclosure includes a CYP24 inhibitor for use in treating or preventing hyperparathyroidism, for example hyperparathyroidism secondary to Chronic Kidney Disease, for example Stage 3 or Stage 4 CKD.

Another aspect of the disclosure includes use of a CYP24 inhibitor for the manufacture of a medicament for treating or preventing vitamin D deficiency.

Another aspect of the disclosure includes use of a CYP24 inhibitor for the manufacture of a medicament for treating or preventing hyperparathyroidism, for example hyperparathyroidism secondary to Chronic Kidney Disease, for example Stage 3 or Stage 4 CKD.

For the compositions, methods, uses, and kits described herein, preferred features, such as components, compositional ranges thereof, substituents, conditions (e.g., characteristics of patient populations), and method steps, can be selected from the various examples provided herein.

Further aspects and advantages will be apparent to those of ordinary skill in the art from a review of the following detailed description, taken in conjunction with the drawings. While the method is susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, nine drawing figures are appended hereto.

DETAILED DESCRIPTION

Figure 1:
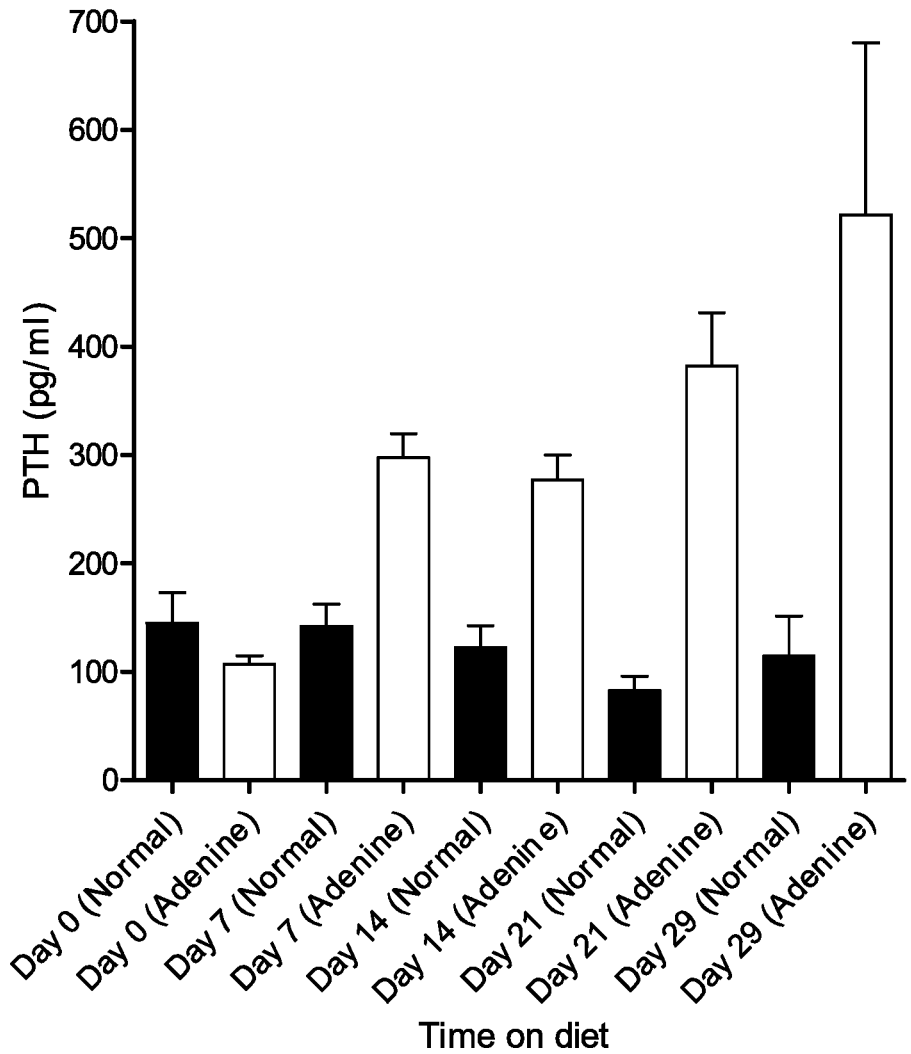
FIG. 1 shows a graph of serum parathyroid hormone (PTH) levels over time in rats fed an adenine-rich diet or a control diet.

"Vitamin D deficiency" is generally defined as a condition in a human patient or other mammal in which serum 25-hydroxyvitamin D levels is below 30 ng/mL (see National Kidney Foundation guidelines, NKF, Am. J. Kidney Dis. 42:S1-S202 (2003), incorporated herein by reference). "Vitamin D deficiency" includes "vitamin D insufficiency," defined as serum 25-hydroxyvitamin D of at least 16 ng/mL and less than 30 ng/mL, "mild" vitamin D deficiency, defined as serum 25-hydroxyvitamin D of 5-15 ng/mL, and "severe" vitamin D deficiency, defined as serum 25-hydroxyvitamin D below 5 ng/mL.

As used herein, the term "vitamin D replete" is defined as a condition in a human patient or other mammal in which serum 25-hydroxyvitamin D levels is at or above 30 ng/mL.

The term "at risk" as used herein generally refers to those patient populations having characteristics or diseases associated with vitamin D deficiency. Specific examples include, but are not limited to, subjects with Stage 1, 2, 3, 4 or 5 chronic kidney disease; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D and also are more likely to stay indoors); chronically or acutely and severely ill adults (who are likely to stay indoors, in hospitals, in intensive care facilities, institutional and assisted-care facilities including subjects with Alzheimer's disease or mentally ill); subjects who cover all exposed skin (such as members of certain religions or cultures); subjects who always use sunscreen (e.g., the application of sunscreen with a Sun Protection Factor (SPF) value of 8 reduces production of vitamin D by 95%, and higher SPF values may further reduce vitamin D); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity, diabetes mellitus, insulin resistance syndrome, endothelial dysfunction (vitamin D deposited in body fat stores is less bioavailable); subjects with osteoporosis; postmenopausal women; individuals with cardiovascular disease, atherosclerosis, and/or heart failure; and/or critically-ill hospitalized subjects.

In one embodiment, the patient does not have cancer. A "cancer" refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a human or animal, or may be a non-tumorigenic cancer cell, such as a leukemia cell. Cancers include, but are not limited to breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal cancer, cervical cancer, a melanoma, uterine or endometrial cancer, cancer of the oral cavity or pharynx, liver cancer, kidney cancer, testis cancer, biliary tract cancer, small bowel or appendix cancer, salivary gland cancer, thyroid gland cancer, adrenal gland cancer, osteosarcoma, and a chondrosarcoma.

As used herein, the term "hyperparathyroidism" refers to one or more of primary hyperparathyroidism, secondary hyperparathyroidism, hyperparathyroidism secondary to chronic kidney disease (Stage 3, 4 or 5) and hyperparathyroidism secondary to vitamin D deficiency.

The terms "subject" and "patient" as used herein generally include humans, mammals (e.g., dogs, cats, rodents, sheep, horses, cows, goats), veterinary animals and zoo animals, preferably humans.

The term "CYP24 expression and/or activity" as used herein generally includes transcription to produce CYP24 mRNA, translation to produce CYP24 protein, and the combination of transcription and translation to produce CYP24 protein, as well as activity of the CYP24 enzyme directly or by calculating the ratio of CYP24 products to CYP24 substrates.

As used herein, the term "vitamin D compound" generally includes vitamin D prehormones (e.g., cholecalciferol and ergocalciferol), vitamin D prohormones (e.g., 1α-hydroxyvitamin $D_3$, 1α-hydroxyvitamin $D_3$, 25-hydroxyvitamin $D_3$, and 25-hydroxyvitamin $D_2$), active vitamin D hormones, analogs of the foregoing, and combinations of any of the foregoing. Specific examples include, but are not limited to, vitamin $D_3$ (cholecalciferol), vitamin $D_2$ (ergocalciferol), 25-hydroxyvitamin $D_3$, 25-hydroxyvitamin $D_2$, 1α,25-dihydroxyvitamin $D_3$, 1α,25-dihydroxyvitamin $D_2$, 1α,25-dihydroxyvitamin $D_4$, and vitamin D analogs (including all hydroxy and dihydroxy forms), including 1,25-dihydroxy-19-nor-vitamin $D_2$, 22-oxacalcitriol, dihydrotachysterol, and 26,26,26,27,27,27-hexafluorocalcitriol (falecalcitriol).

As used herein, the terms "active vitamin D" and "activated vitamin D" refer to a vitamin D compound that is hydroxylated in at least the 1α position. Active vitamin D compounds include calcitriol, 1,25-dihydroxyvitamin $D_2$, alfacalcidol, doxercalciferol, 22-oxacalcitriol, and paricalcitol.

As used herein, the phrase "therapeutically effective amount" refers to an amount of therapeutic or prophylactic agent (e.g., a CYP24 inhibitor or dual action CYP24 inhibitor and VDR agonist) that would be appropriate for an embodiment of the present invention, and that will elicit the desired therapeutic or prophylactic effect or response when administered in accordance with the desired treatment regimen. More specifically, a "therapeutically effective amount" means an amount effective to prevent development of, to eliminate, to correct, or to retard the progression of the relevant condition, e.g. vitamin D deficiency. Determination of a therapeutically effective amount is well within the capability of those skilled in the art, especially in light of the detailed disclosure provided herein.

A "therapeutically effective dose" refers to that amount of the active ingredients that results in achieving the desired effect. Toxicity and therapeutic efficacy of such active ingredients can be determined by standard pharmaceutical procedures in cell cultures or experimental animals, e.g., determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. A high therapeutic index is preferred. The data obtained can be used in formulating a range of dosage for use in humans. The dosage of the active ingredients preferably lies within a range of circulating concentrations that include the $ED_{50}$ with little or no toxicity. The dosage can vary within this range depending upon the dosage form employed, and the route of administration utilized.

As used herein, the term "comprising" indicates the potential inclusion of other agents, elements, steps, or features, in addition to those specified.

One aspect of the disclosure provides a method for diagnosing catabolism-related vitamin D deficiency. The method includes measuring CYP24 expression and/or activity in a vitamin D deficient patient and correlating abnormally elevated CYP24 expression and/or activity with catabolism-related vitamin D deficiency. In response to abnormally elevated CYP24 expression and/or activity, the method can further include administering a CYP24 inhibitor to the vitamin D deficient patient.

Another aspect of the disclosure provides a method for diagnosing susceptibility for catabolism-related vitamin D deficiency. The method includes measuring CYP24 expression and/or activity in a patient and correlating abnormally elevated CYP24 expression and/or activity with susceptibility for catabolism-related vitamin D deficiency. In response to abnormally elevated CYP24 expression and/or activity in a vitamin D replete patient, the method can further include inhibiting and/or preventing vitamin D deficiency by administering a CYP24 inhibitor to the vitamin D replete patient. In response to abnormally elevated CYP24 expression and/or activity in a vitamin D deficient patient, the method can further include treating vitamin D deficiency by administering a CYP24 inhibitor to the vitamin D deficient patient.

Yet another aspect of the disclosure provides a method for treating or preventing vitamin D deficiency and/or hyperparathyroidism. The method includes measuring CYP24 expression and/or activity in a patient, or a proxy therefor, and administering a CYP24 inhibitor to the patient in response to abnormally elevated CYP24 expression and/or activity. The method can include treating vitamin D deficiency by administering the CYP24 inhibitor to a vitamin D deficient patient having abnormally elevated CYP24 expression and/or activity. The method can further include inhibiting and/or preventing vitamin D deficiency by administering the CYP24 inhibitor to a vitamin D replete patient having abnormally elevated CYP24 expression and/or activity. The method can include inhibiting and/or preventing hyperparathyroidism by administering the CYP24 inhibitor to a patient having abnormally elevated CYP24 expression and/or activity. The method can also include inhibiting and/or preventing a deficiency of 1,25-dihydroxyvitamin D by administering the CYP24 inhibitor to a patient having abnormally elevated CYP24 expression and/or activity.

Another aspect of the disclosure provides a method for treating or preventing vitamin D deficiency in a patient. The method includes measuring CYP24 expression and/or activity in the patient and administering a CYP24 inhibitor to the patient in response to abnormally elevated CYP24 expression and/or activity. The method further includes avoiding exacerbation of increased CYP24 levels and vitamin D deficiency in the patient in response to abnormally elevated CYP24 expression and/or activity, e.g. by reducing, avoiding (omitting), or ceasing activation of the vitamin D binding receptor (VDR) by outside influences, for example by reducing, avoiding (omitting), or ceasing administration of active vitamin D compounds. The method can further include administering a vitamin D supplement to the patient, such as by administering 25-hydroxyvitamin D (e.g., 25-hydroxyvitamin $D_3$) to the patient. The method can further include measuring the intact parathyroid hormone (PTH) levels and 25-hydroxyvitamin D levels in the patient. In one embodiment, the patient has abnormally elevated PTH level and normal 25-hydroxyvitamin D level. In another embodiment, the patient has abnormally elevated PTH levels and abnormally decreased 25-hydroxyvitamin D level (e.g., vitamin D deficiency). In another embodiment, the patient has normal PTH levels and abnormally decreased 25-hydroxyvitamin D levels. The method can further include measuring glomerular filtration rate (GFR) in the patient to determine the Stage of Chronic Kidney Disease. In one embodiment, the patient will have CKD selected from stages 1-5. In another embodiment, the patient will have CKD selected from stages 1 and 2. In another embodiment, the patient will have CKD selected from stages 3 and 4.

One embodiment of the disclosure provides for measuring CYP24 activity by measuring the level of fibroblast growth factor-23 (FGF23) in a patient. Another embodiment provides for measuring CYP24 expression and/or activity by measuring the level of one or more catabolic byproducts of CYP24 (including but not limited to, 24,25-dihydroxyvitamin $D_3$, 25-hydroxyvitamin $D_3$-26,23-lactone, 1,24,25-trihydroxyvitamin $D_3$, 24,25-dihydroxyvitamin $D_2$, or 1,24,25-trihydroxyvitamin $D_2$ or the terminal products of CYP24 activity on vitamin D3 metabolites including calcitroic acid or 1,25-$(OH)_2D_3$-26,23-lactone). Another embodiment provides for measuring CYP24 activity by measuring ratios of one or more catabolic byproducts of CYP24 to one or more corresponding precursors (e.g. the ratio of 24,25-dihydroxyvitamin D to 25-hydroxyvitamin D, or the ratio of 1,24,25-trihydroxyvitamin D to 1,25-dihydroxyvitamin D). Still other embodiments provide for measuring CYP24 expression by measuring the level of CYP24 mRNA in a patient, the level of CYP24 protein in a patient, and/or the level of CYP24 enzyme activity in a patient. Another embodiment provides for measuring CYP24 activity by measuring CYP24 metabolite(s) of other CYP24 substrates which could be introduced (e.g., by injection), metabolized by CYP24, and then measured.

Another aspect of the disclosure provides a kit for diagnosing catabolism-related vitamin D deficiency. In one embodiment, the kit includes an assay or other apparatus for measuring CYP24 mRNA, protein or enzymatic activity, and instructions for use, for example according to a method disclosed herein.

The diagnostic kit and methods disclosed herein are contemplated to include embodiments including any combination of one or more of the additional optional elements, features, and steps further described below (including those shown in the figures), unless stated otherwise.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

In one aspect, the present disclosure provides a method of diagnosing catabolism-related vitamin D deficiency. The method includes measuring CYP24 expression and/or activity in a vitamin D deficient patient and correlating abnormally elevated CYP24 expression and/or activity with catabolism-related vitamin D deficiency. In response to abnormally elevated CYP24 expression and/or activity, the method can further include administering a CYP24 inhibitor to the vitamin D deficient patient.

In another aspect, the present disclosure provides a method of diagnosing susceptibility for catabolism-related vitamin D deficiency. The method includes measuring CYP24 expression and/or activity in a patient and correlating abnormally elevated CYP24 expression and/or activity with susceptibility for catabolism-related vitamin D deficiency. In response to abnormally elevated CYP24 expression and/or activity in a vitamin D replete patient, the method can further include inhibiting and/or preventing vitamin D deficiency by administering a CYP24 inhibitor to the vitamin D replete patient. In response to abnormally elevated CYP24 expression and/or activity in a vitamin D deficient patient, the method can further include treating vitamin D deficiency by administering a CYP24 inhibitor to the vitamin D deficient patient.

In yet another aspect, the present disclosure provides a method of treating or preventing vitamin D deficiency and/or hyperparathyroidism. The method includes measuring CYP24 expression and/or activity, or a proxy therefor, in a patient and administering a CYP24 inhibitor to the patient in response to abnormally elevated CYP24 expression and/or activity. The method can include treating vitamin D deficiency by administering the CYP24 inhibitor to a vitamin D deficient patient having abnormally elevated CYP24 expression and/or activity. The method can include inhibiting and/or preventing vitamin D deficiency by administering the CYP24 inhibitor to a vitamin D replete patient having abnormally elevated CYP24 expression and/or activity. The method can include inhibiting and/or preventing hyperparathyroidism by administering the CYP24 inhibitor to a patient having abnormally elevated CYP24 expression and/or activity. The method can also include inhibiting and/or preventing a deficiency of 1,25-dihydroxyvitamin D by administering the CYP24 inhibitor to a patient having abnormally elevated CYP24 expression and/or activity.

Vitamin D deficiency is associated with a host of additional diseases and disorders, including secondary hyperparathyroidism, parathyroid gland hyperplasia, hypocalcemia, psoriasis, chronic kidney disease (CKD), and metabolic bone diseases such as fibrogenesis imperfecta ossium, osteitis fibrosa cystica, osteomalacia, rickets, osteoporosis, osteopenia, osteosclerosis, renal osteodystrophy, and extraskeletal calcification. The methods in accordance with the present disclosure also are useful for treating or preventing diseases or disorders associated with vitamin D deficiency.

The current standard of care for CKD patients states that patients should have their PTH and 25-hydroxyvitamin D levels measured. In Stage 3 and Stage 4 patients, if the plasma intact parathyroid (PTH) level is elevated (e.g., above the target range for the stage of CKD) and the 25-hydroxyvitamin D is decreased (<30 ng/ml), then the patient is treated with a vitamin $D_2$ supplement (ergocalciferol). See "Guideline 7: Prevention And Treatment Of Vitamin D Insufficiency And Vitamin D Deficiency In People With CKD (Algorithm 1)" of National Kidney Foundation K/DOQI clinical practice guidelines for bone metabolism and disease in chronic kidney disease, Am J Kidney Dis 42:S1-S202, 2003 (Suppl 3), incorporated herein by reference. For CKD Stage 3 (GFR Range 30-59 ml/min/1.73 m$^2$), the target PTH level is 35-70 pg/ml (3.85-7.7 pmol/L). For CKD Stage 4 (GFR Range 15-29 ml/min/1.73 m$^2$), the target PTH level is 70-110 pg/ml (7.7-12.1 pmol/L).

On the other hand, if the PTH level is above the target range for the stage of CKD and the serum levels of 25-hydroxyvitamin D are >30 ng/ml, then the patient is treated with an active vitamin D hormone (e.g., calcitriol, alfacalcidol, or doxercalciferol). See "Guideline 8A: Active Vitamin D Therapy In Stages 3 And 4 CKD (Algorithm 2)" of National Kidney Foundation K/DOQI clinical practice guidelines for bone metabolism and disease in chronic kidney disease, Am J Kidney Dis 42:S1-S202, 2003 (Suppl 3), incorporated herein by reference.

Figure 12:
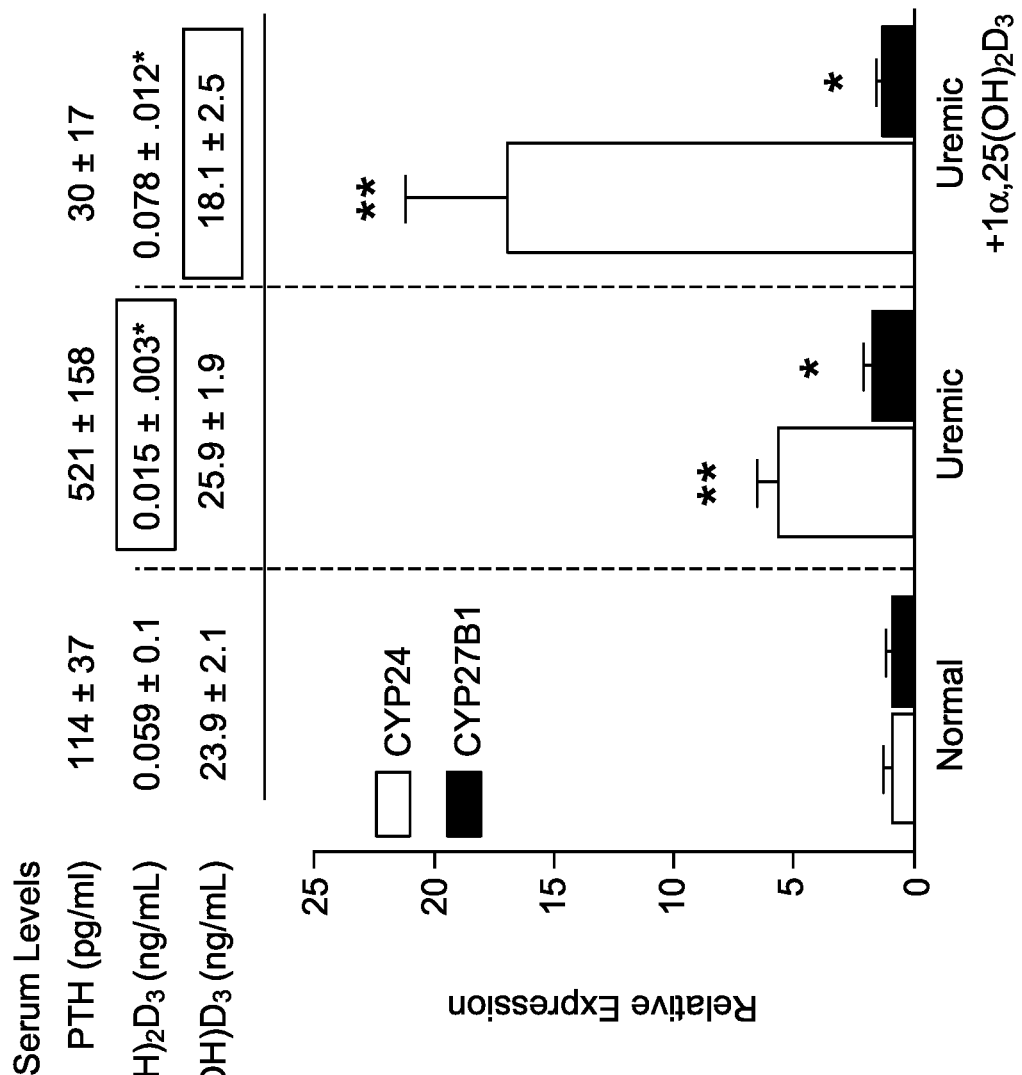
FIG. 12 shows relative expression of CYP24 and CYP27B1 in normal rats, adenine-induced uremic rats, and adenine-induced uremic rats treated with 1,25-dihydroxyvitamin $D_3$, with resultant exacerbation of vitamin D deficiency.

Without intending to be bound by any particular theory, FIG. 12 shows that if the level of 25-hydroxyvitamin D is normal, treating with an active vitamin D hormone per guidelines will increase the levels of CYP24, and therefore will exacerbate vitamin D deficiency despite reducing PTH levels. In patients with chronic kidney disease and elevated PTH levels, CYP24 overactivity should be managed by (a) using a CYP24 inhibitor and/or (b) avoiding further exacerbation of increased CYP24 levels and vitamin D deficiency.

Accordingly, another aspect of the disclosure provides a method for treating or preventing hyperparathyroidism secondary to chronic kidney disease (preferably Stages 3 and 4) in a patient. The method includes measuring CYP24 expression and/or activity in the patient and administering a CYP24 inhibitor to the patient in response to abnormally elevated CYP24 expression and/or activity. The method preferably further includes avoiding exacerbation of increased CYP24 levels and vitamin D deficiency, if present, by avoiding administration of active vitamin D. The method can further include administering vitamin D supplementation to the patient, preferably with 25-hydroxyvitamin D (e.g., 25-hydroxyvitamin $D_3$). The method can further include measuring 25-hydroxyvitamin D level in the patient. In one embodiment, the patient has abnormally elevated PTH levels and normal 25-hydroxyvitamin D levels. In another embodiment, the patient has abnormally elevated PTH levels and abnormally decreased 25-hydroxyvitamin D levels. In yet another embodiment, the patient has normal PTH levels and abnormally decreased 25-hydroxyvitamin D levels. The method can further include measuring glomerular filtration rate (GFR) in the patient to determine the stage of the chronic kidney disease.

In one embodiment, and without intending to be bound by any particular theory, FGF23 level is used as a proxy for CYP24 expression and/or activity. In another embodiment, and without intending to be bound by any particular theory, elevated FGF23 itself is a marker for susceptibility to vitamin D deficiency, without respect to any particular mechanism of causation (i.e., whether through catabolism by CYP24, or not). The level of FGF23 in a biological sample obtained from a patient can be determined by a variety of techniques known to one skilled in the art. For example, concentrations of intact FGF-23 (iFGF23) and median C-terminal FGF-23 (cFGF23) can be measured using ELISA kits available from IMMUTOPICS (San Clemente, Calif., USA). Measurements of the foregoing species are preferably made as serum concentrations, although concentrations can be measured in plasma, serum or other bodily fluids (e.g., saliva) or tissues. Normal iFGF23 levels are in the range of 0 to 90 pg/mL for healthy adult humans (Fliser et al. *J. Am. Soc. Nephrol.* 18:2601-2608 (2007), Ibrahim et al. *Int. Urol. Nephrol.* 41(1):163-169 (2009)). Normal cFGF23 levels are in the range of 0 to 85 reference units (RU)/mL for healthy adult humans (Tebbin et al. *Mayo Clin. Proc.* 80(6):745-751 (2005)). A level of FGF23 greater than the upper value of the normal range would be indicative of abnormally elevated CYP24 expression. The further the level of FGF23 is from the upper end of the normal range, the greater the correlation to abnormally elevated CYP24 expression. Elevated FGF23 according to the methods described herein will be at least 2-fold greater than normal, for example 3-fold, 4-fold, 5-fold, 10-fold, 50-fold, 100-fold, or 1000-fold.

In another embodiment, CYP24 activity is measured by measuring the level of one or more catabolic byproducts of CYP24. The level of catabolic byproducts of CYP24 in a biological sample obtained from a patient can be determined by a variety of techniques known to one skilled in the art. For example, CYP24 catabolic byproducts can be measured by immunoassays such as enzyme-linked immunosorbent assays (ELISAs), radioimmunoassays (RIAs), immunofluorescent assays, and the like. Another approach to measure CYP24 byproducts such as 25-hydroxyvitamin $D_3$-26,23-lactone or 1,25-dihydroxyvitamin $D_3$-26,23-lactone would take advantage of their high affinity to natural vitamin D binding proteins such as vitamin D binding protein (DBP) or vitamin D receptor. Such proteins also can be modified by methods known to one skilled in the art to have greater affinity or selectivity for such vitamin D products. Synthetic antibodies or proteins having affinity for vitamin D metabolites of interest could also be generated using techniques such as phage-display or yeast display and could be incorporated into a kit to determine vitamin D metabolite and CYP24 catabolic byproduct concentration. Other techniques to measure CYP24 catabolic byproducts include high performance liquid chromatography (HPLC) in combination with UV-visible spectroscopy, fluorescence spectroscopy, mass spectrometry, and the like. CYP24 activity also can be measured by measuring ratios of one or more catabolic byproducts of CYP24 to one or more corresponding precursors. CYP24 catabolic byproducts include 24-hydroxylated natural and synthetic vitamin D compounds. Examples of natural CYP24 catabolic byproducts include 24,25-dihydroxyvitamin $D_3$, 1,24,25-trihydroxyvitamin $D_3$, 24,25-dihydroxyvitamin $D_2$, and 1,24,25-trihydroxyvitamin $D_2$. Additional products of CYP24 can also be 23-hydroxylated such as the 25-hydroxyvitamin $D_3$-26,23-lactone or the 1,25-dihydroxyvitamin $D_3$-26,23-lactone. Additional examples of CYP24 catabolic byproducts include the products obtained by 24-hydroxylation of synthetic vitamin D compounds. Synthetic vitamin D compounds include paricalcitol (ZEMPLAR®), doxercalciferol (HECTOROL®), 22-oxacalcitriol, alfacalcidol, and 26,26,26,27,27,27-hexafluorocalcitriol (falecalcitriol). Measurements of the foregoing species are preferably made as serum concentrations, although concentrations can be measured in serum or other bodily fluids (e.g., saliva). Measurements can be made after acute or chronic administration of a CYP24 substrate.

The corresponding precursor compounds of CYP24 catabolic byproducts include, for example, 25-hydroxyvitamin $D_3$, 1,25-dihydroxyvitamin $D_3$, 25-hydroxyvitamin $D_2$, and 1,25-dihydroxyvitamin $D_2$. The level of corresponding precursor compounds can be measured along with CYP24 catabolic byproducts, and ratios of one or more catabolic byproducts of CYP24 to one or more corresponding precursors can be used to obtain a value for CYP24 activity. For example, ratios including 24,25-dihydroxyvitamin D to 25-hydroxyvitamin D and 1,24,25-trihydroxyvitamin D to 1,25-dihydroxyvitamin D can be measured and used to obtain CYP24 activity. Measurements of the foregoing species are preferably made as serum concentrations, although concentrations can be measured in serum or other bodily fluids (e.g., saliva). Measurements can be made after acute or chronic administration of a CYP24 substrate.

In another embodiment, CYP24 expression is determined by measuring the level of CYP24 mRNA in a patient. The level of mRNA in a biological sample obtained from a patient can be determined by a variety of techniques known to one skilled in the art. In Northern blotting, for example, mRNA levels can be quantified by hybridizing radioactively- or fluorescently-labeled probes with mRNA samples that have been separated by electrophoresis and/or bound to a membrane or other solid support. DNA microarray technologies provide another means for quantifying mRNA levels, whereby a fluorescently-labeled mRNA sample is allowed to hybridize with tens to hundreds of thousands of DNA oligonucleotides affixed to a solid support in a defined pattern. Techniques that provide signal amplification are particularly useful when low levels of mRNA are present. For example, quantitative real time-polymerase chain reaction (qRT-PCR) provides mRNA quantification by conversion of the target mRNA to the corresponding DNA molecule, followed by amplification via the polymerase chain reaction. By using a fluorescently labeled primer, mRNA levels can be monitored in real-time during the amplification process.

In another embodiment, CYP24 expression is determined by measuring the level of CYP24 protein in a patient. The level of protein in a biological sample obtained from a patient can be determined by a variety of techniques known to one skilled in the art. In Western blotting, for example, protein levels can be quantified by detecting the binding of an antibody specific for the target protein with protein samples that have been separated by electrophoresis and/or bound to a membrane or other solid support. Assays that rely on the binding of a specific antibody to a target antigen (e.g. CYP24) can take a variety of forms, and in addition to Western blotting (immunoblotting), examples of such assays include enzyme-linked immunosorbent assays (ELISAs), radioimmunoassays (RIAs), immunofluorescent assays, and the like. Protein levels also can be measured by various staining, spectroscopic, and spectrometric detection techniques, optionally in combination with various separation techniques. Examples of detection techniques include Coomassie staining, silver staining, UV-visible spectroscopy, fluorescence spectroscopy, mass spectrometry, and the like. These detection techniques can be combined with separation techniques, such as electrophoresis, capillary electrophoresis, high performance liquid chromatography (HPLC), fast protein liquid chromatography (FPLC), thin layer chromatography (TLC), Luminex® xMAP® multiplexing technology for gene quantification, and the like.

In yet another embodiment, CYP24 activity is measured by measuring the level of CYP24 enzyme activity in a patient. The level of enzymatic activity in a biological sample obtained from a patient can be determined by a variety of techniques known to one skilled in the art. In the case of CYP24, enzymatic activity can be measured by measuring the conversion of 25-hydroxyvitamin $D_3$ to the corresponding 24-hydroxylated product. For example, conversion of 25-hydroxyvitamin $D_3$ to 24,25-dihydroxyvitamin $D_3$ can be assessed by incubating a biological sample from a patient with a radioactively-labeled 25-hydroxyvitamin $D_3$ substrate, separating the reaction products by HPLC, and measuring the radioactivity of the 24,25-dihydroxyvitamin $D_3$ peak compared to the total radioactivity.

In one aspect, CYP24 expression and/or activity can be measured in one or more of tissues, plasma, and cells of a vitamin D deficient or vitamin D replete patient. CYP24 expression and/or activity can be measured in tissues obtained by a tissue biopsy, and can include tissues such as, but not limited to, skin tissue, kidney tissue, liver tissue, parathyroid gland tissue, and the like. In one embodiment, kidney tissue is preferred. In another embodiment, parathyroid gland tissue is preferred. CYP24 expression and/or activity also can be measured in cells, including cells obtained from the blood, such as peripheral blood mononuclear cells, and cells obtained from swabs of tissues, such as buccal cells. In one embodiment of the methods herein, CYP24 expression and/or activity is measured by a systemic indicator (e.g. peripheral blood mononuclear cells or serum), in preference to a tissue-based measurement of overexpression, which can occur in tumor growth.

In one aspect, CYP24 expression and/or activity is abnormally elevated. Normal levels of CYP24 expression and/or activity are defined as 1 relative unit (RU) measured based on the mean value of CYP24 expression and/or activity from 50-100 "normal" donors where CYP24 mRNA has been prepared and used as a reference.

The basal level for CYP24 can be established from samples (e.g. kidney, skin, blood, serum, plasma, saliva, buccal swab) collected in normal individuals from various population groups based on, for example, gender, ethnicity, and/or age. CYP24 RNA level can be established from tissues (e.g. kidney or skin biopsy) or cells (e.g. buccal swab) by real-time PCR, Luminex® xMAP® multiplexing technology, or another technique. CYP24 protein level will be measured in these tissues by using techniques such as Luminex® xMAP® multiplexing technology and Westernblot. The mean value for the CYP24 RNA level or the CYP24 protein level will be recorded as 1 RU.

The normal levels of 24-hydroxylated natural and synthetic vitamin D compounds such as 24,25-dihydroxyvitamin $D_3$, 1,24,25-trihydroxyvitamin $D_3$ or lactones can be established from samples (e.g. blood, plasma, saliva) in absolute quantity based on a standard curve using techniques such as HPLC, gas chromatography, mass spectrometry, and methods previously cited. The absolute values of the 24-hydroxylated natural and synthetic vitamin D compounds will be used as the normal levels by the physician.

If the level of CYP24 RNA, the level of CYP24 protein, or the absolute value of a 24-hydroxylated natural or synthetic vitamin D compound in a patient falls outside of the "normal" range, the patient has abnormally elevated CYP24 expression and/or activity. For example CYP24 expression and/or activity can be at least 2-fold increased over normal CYP24 expression and/or activity, at least 3-fold increased, at least 4-fold increased, at least 5-fold increased, or at least 10-fold increased over normal CYP24 expression and/or activity. It is contemplated that abnormally elevated CYP24 expression and/or activity could be as much as hundreds or thousands of times increased over normal CYP24 expression and/or activity (e.g., 100×, 500×, 1000×, 5000×, etc.).

In one embodiment, a physician will determine if a patient has abnormally elevated CYP24 expression and/or activity by collecting at least one sample (e.g. blood, plasma, saliva, serum, buccal swab) from the patient and measuring the level of CYP24 RNA, the level of CYP24 protein, or the absolute value of a 24-hydroxylated natural or synthetic vitamin D compound. If one or several measured parameters falls outside of the "normal" range, and preferably at least 2-fold, 3-fold, 4-fold increased, etc., as described above, the physician will diagnose the patient as having abnormally elevated CYP24 activity and/or expression and may prescribe a CYP24 inhibitor.

CYP24 inhibitors can include organic molecules, single-stranded or double-stranded nucleic acids (e.g. sense, anti-sense, or missense oligonucleotides; aptamers; sense, anti-sense, or missense polynucleotides; sense, anti-sense, or missense DNA; sense, anti-sense, or missense RNA; and siRNA), peptides, carbohydrates, and proteins (e.g. antibodies, antibody fragments, hormones, hormone analogs, glycoproteins, and lectins). In one embodiment, the CYP24 inhibitor comprises the compound disclosed as Formula IX (Compound 1) in U.S. Pat. No. 6,380,408 (col. 6), which is (5Z,7E,16Z,23E)-(1S,3R)-25-nor-25-t-butylsulfonyl-9,10-seco-5,7,10(19),16,23-cholestapentaene-1,3-diol. In another embodiment, the CYP24 inhibitor comprises an azole compound such as, for example, (R)—N-(2-(1H-imidazol-1-yl)-2-phenylethyl)-4'-chlorobiphenyl-4-carboxamide, ketoconazole, metronidazole, clomethiazole, itraconazole, and fluconazole.

One class of organic molecule inhibitors of CYP24 includes analogs of vitamin D compounds. Examples of 1α,25-dihydroxyvitamin $D_3$ analogs which have CYP-24 inhibition activity are disclosed in U.S. Pat. Nos. 6,380,408; 7,101,865; 7,166,585; and 6,982,258, and U.S. patent application Ser. No. 10/738,248, incorporated herein by reference in their entirety, and include 23,23-difluoro-24-sulfone vitamin $D_3$ compounds, 25-sulfone vitamin $D_3$ compounds, 24,24-difluoro-25-sulfone vitamin $D_3$ compounds, 24-sulfoximine vitamin $D_3$ compounds, 16-ene-25-oxime vitamin $D_3$ compounds, and 16-ene-25-oxime ether vitamin $D_3$ compounds, 24-sulfone vitamin $D_3$ compounds, and 24,24-difluoro vitamin $D_3$ compounds. In one aspect of the method, the molecule can be selected from pure CYP24 inhibitors, for example (5Z,7E)-(1S,3R)-24-(S)-phenylsulfoximine-25-nor-9,10-seco-5,7,10(19)-cholestatriene-1,3-diol (see U.S. Pat. No. 7,101,865, Compound I(a)). In another aspect of the method, the molecule can be selected from compounds which are both CYP24 inhibitors and vitamin D agonists, for example (5Z,7E,16Z,23E)-25-nor-25-t-butylsulfonyl-9,10-seco-5,7,10(19),16,23-cholestapentaene-1,3β-diol (see U.S. Pat. No. 6,380,408, Formula IX, Compound 1) and (5Z,7E,16Z)-(1S,3R)-25-(O-allyl)-N-t-butyloxime-9,10-seco-5,7,10(19),16-cholestatetraene-1,3β-diol (see U.S. Pat. No. 6,982,258, Compound I(g)).

CYP24 inhibitors optionally can be administered in combination with other agents that increase vitamin D levels in the body. Agents known in the art to increase vitamin D levels in the body are encompassed by the present disclosure and include, for example, vitamin $D_2$, 25-hydroxyvitamin $D_2$, 1,25-dihydroxyvitamin $D_2$, vitamin $D_3$, 25-hydroxyvitamin $D_3$, and 1,25-dihydroxyvitamin $D_3$. Preferably, active vitamin D compounds are avoided in favor of vitamin D prehormones, vitamin D prohormones, and analogs thereof.

Both cholecalciferol and ergocalciferol are metabolized into prohormones by enzymes primarily located in the liver of the human body. Cholecalciferol is metabolized into a prohormone 25-hydroxyvitamin $D_3$, and ergocalciferol is metabolized into two prohormones, 25-hydroxyvitamin $D_2$ and 24(S)-hydroxyvitamin $D_2$. Cholecalciferol and ergocalciferol also can be metabolized into prohormones outside of the liver in certain cells, such as enterocytes, by enzymes which are identical or similar to those found in the liver. Elevating concentrations of either precursor increases prohormone production; similarly, lowering precursor concentrations decreases hormone production. Surges in the blood levels of cholecalciferol and/or ergocalciferol ("cholecalciferol/ergocalciferol") can transiently raise intracellular Vitamin D concentrations, accelerating prohormone production and elevating intracellular and blood prohormone concentrations.

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular vitamin D receptors and secrete PTH. The secreted PTH stimulates expression of renal CYP27B1 and, thereby, increases production of vitamin D hormones. As blood concentrations of 1,25-dihydroxyvitamin D rise again, the parathyroid glands attenuate further PTH secretion. As blood PTH levels fall, renal production of vitamin D hormones decreases. Rising blood levels of 1,25-dihydroxyvitamin D also directly inhibit further vitamin D hormone production by CYP27B1.

Substantial surges in the blood levels of cholecalciferol, ergocalciferol, and 25-hydroxyvitamin D also can cause up-regulation of CYP24 as a response, to catabolize the transitory excess of vitamin D substrates. Similarly, rising blood levels of 1,25-dihydroxyvitamin D can cause up-regulation of CYP24 activity.

Without intending to be bound by any particular mode of operation, it is believed that overexpression of CYP24 is the cause of at least some forms of vitamin D deficiency, operating independently of, but potentially complicated by, deficiencies in substrates and/or sunlight.

Accordingly, in one type of embodiment of the methods disclosed herein, a CYP24 inhibitor will be administered alone, or without administration of a vitamin D compound (e.g. cholecalciferol, ergocalciferol, vitamin D prohormone, vitamin D hormone, or analogs thereof), most preferably without administration of an active vitamin D hormone or analog thereof. In another embodiment of the methods disclosed herein, a CYP24 inhibitor will be administered alone, or when a vitamin D compound (e.g. cholecalciferol, ergocalciferol, vitamin D prohormone, vitamin D hormone, or analogs thereof) is also administered, the vitamin D compound will be administered in a modified release formulation to avoid surges in blood levels of the compound (e.g. a sustained or extended release formulation), or via a slow-push IV delivery method.

In one aspect, the present disclosure provides a kit for diagnosing catabolism-related vitamin D deficiency. The kits in accordance with the present disclosure provide a measure of CYP24 expression and/or activity, and include kits measuring one or more properties including levels of CYP24 catabolic byproducts or precursors to the catalytic byproducts, levels of CYP24 mRNA, levels of CYP24 protein, and/or levels of CYP24 enzyme activity. In one embodiment, the kit includes an immobilized anti-CYP24 antibody, a labeled anti-CYP24 antibody, and instructions for use, for example according to a method disclosed herein. Other kits involving antibody-based detection are also contemplated by the present disclosure. For example, kits for measuring CYP24 expression can measure the level of CYP24 catabolic byproducts. The kits can include an assay for measuring the levels of one or more corresponding precursors to the catalytic byproducts. One such kit can include an antibody (or functional fragments thereof) specific for a CYP24 catabolic byproduct, and an antibody specific for vitamin D compounds including CYP24 catabolic byproducts. Proteins with high affinity for vitamin D metabolites and CYP24 catabolic byproducts such as DBP or VDR or synthetically derived proteins or macromolecules can also be contemplated for use in place of the antibody in such kits. It is contemplated that one of the aforementioned antibodies is immobilized to a solid support and the other antibody possesses a label for detection. In another example, a kit for measuring CYP24 expression can include an immobilized CYP24 catabolic byproduct, and an anti-CYP24 antibody. CYP24 activity is measured with the aforementioned kit by measuring the ability of CYP24 catabolic byproducts to compete with the immobilized CYP24 catabolic byproduct for binding to the anti-CYP24 antibody.

In another aspect, the disclosure includes a pharmaceutical formulation for treating or preventing vitamin D deficiency including an effective amount of a CYP24 inhibitor. The formulation can further include an effective amount of 25-hydroxyvitamin $D_3$.

In yet another aspect, the disclosure includes a pharmaceutical formulation for treating or preventing hyperparathyroidism including an effective amount of a CYP24 inhibitor. The formulation can further include an effective amount of 25-hydroxyvitamin $D_3$. The pharmaceutical formulation can be for treating hyperparathyroidism secondary to Chronic Kidney Disease, for example Stage 1 or Stage 2 CKD.

The exact formulation, route of administration, and dosage is determined by an individual physician in view of the patient's condition. Dosage amounts and intervals can be adjusted individually to provide levels of the active ingredients that are sufficient to maintain therapeutic or prophylactic effects.

Such formulations can be in the form of, for example, granules, powders, tablets, capsules, syrup, suppositories, injections, emulsions, elixirs, suspensions or solutions. The instant formulations can be formulated for various routes of administration, for example, by oral administration, by nasal administration, by rectal administration, subcutaneous injection, intravenous injection, intramuscular injections, or intraperitoneal injection. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more of the CYP24 inhibitors or dual action CYP24 inhibitor and VDR agonist of the instant invention with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or antioxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For nasal administration, the pharmaceutical formulations and medicaments may be a spray or aerosol containing an appropriate solvent(s) and optionally other compounds such as, but not limited to, stabilizers, antimicrobial agents, antioxidants, pH modifiers, surfactants, bioavailability modifiers and combinations of these. A propellant for an aerosol formulation may include compressed air, nitrogen, carbon dioxide, or a hydrocarbon based low boiling solvent.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is nonvolatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

For rectal administration, the pharmaceutical formulations and medicaments may be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

The formulations of the invention may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention.

Besides those representative dosage forms described above, pharmaceutically acceptable excipients and carries are generally known to those skilled in the art and are thus included in the instant invention. Such excipients and carriers are described, for example, in "Remington's Pharmaceutical Sciences" Mack Pub. Co., New Jersey (1991), which is incorporated herein by reference.

Suitable modified release formulations for vitamin D compounds are disclosed in application PCT/US2008/061579, published as WIPO publication WO 2008/134512 (Nov. 6, 2008), and the disclosure thereof is incorporated herein by reference. It is contemplated that such formulations can also include compatible CYP24 inhibitors and dual-action CYP23 inhibitors and VDR agonists.

EXAMPLES

The following examples are provided for illustration and are not intended to limit the scope of the invention.

The Examples below support the following conclusions.

CYP24 gene expression is strongly induced by 1,25-dihydroxyvitamin $D_3$ in tissues from both normal and uremic rats.

Constitutive expression of CYP24 is relatively higher in healthy kidney compared to other tissues. In uremic rats, however, basal expression of CYP24 is markedly elevated. This suggests that mechanisms associated with the uremic state may be involved in regulating CYP24 expression.

CYP24 is significantly induced by 1,25-dihydroxyvitamin $D_3$ in parathyroid glands of uremic animals compared to those from normal animals, suggesting that repeated dosing may lead to increased resistance.

Expression of CYP27B1 in uremic rats does not correlate with diminished levels of 1,25-dihydroxyvitamin $D_3$, suggesting a more prominent role for CYP24 in lowering vitamin D levels in uremia.

In normal animals, CYP24 expression is dependent upon vitamin D status; vitamin D deficiency markedly decreases CYP24 expression levels. Uremic animals exhibit higher basal levels of CYP24 expression which do not change in a state of vitamin D deficiency. This suggests that in uremia, mechanisms independent of vitamin D regulate CYP24 levels. This may have an impact on vitamin D status in uremia.

Elevated basal expression of CYP24 in the uremic kidney may be a significant mechanism contributing to underlying 25(OH)$D_3$ and 1,25-dihydroxyvitamin $D_3$ deficiency and resistance to vitamin D hormone replacement therapy. Compounds which inhibit CYP24 may be useful in maintaining vitamin D status and overcoming CYP24 resistance to therapy.

FGF23 synergizes with 1,25-dihydroxyvitamin D to induce CYP24 RNA production. In a uremic situation, a high level of FGF23 might contribute to further elevate CYP24, making a patient resistant to vitamin D treatment.

CYP24 levels decrease in vitamin D deficient animals and increase to normal or higher levels after treatment with 25-hydroxyvitamin D.

CYP24 levels do not change in uremic vitamin D deficient rats and do not increase after treatment with 25-hydroxyvitamin D, which suggests a loss of vitamin D control in uremic rats.

In vitamin D deficient uremic rats, CYP24 RNA levels are elevated compared to vitamin D deficient animals. This can explain why, after dosing with 25-hydroxyvitamin $D_3$ for two weeks, the levels of 1,25-dihydroxyvitamin $D_3$ are lower in vitamin D deficient uremic rats compared to vitamin D deficient animals.

Example 1

Animal Model of Vitamin D Deficiency

Figure 2:
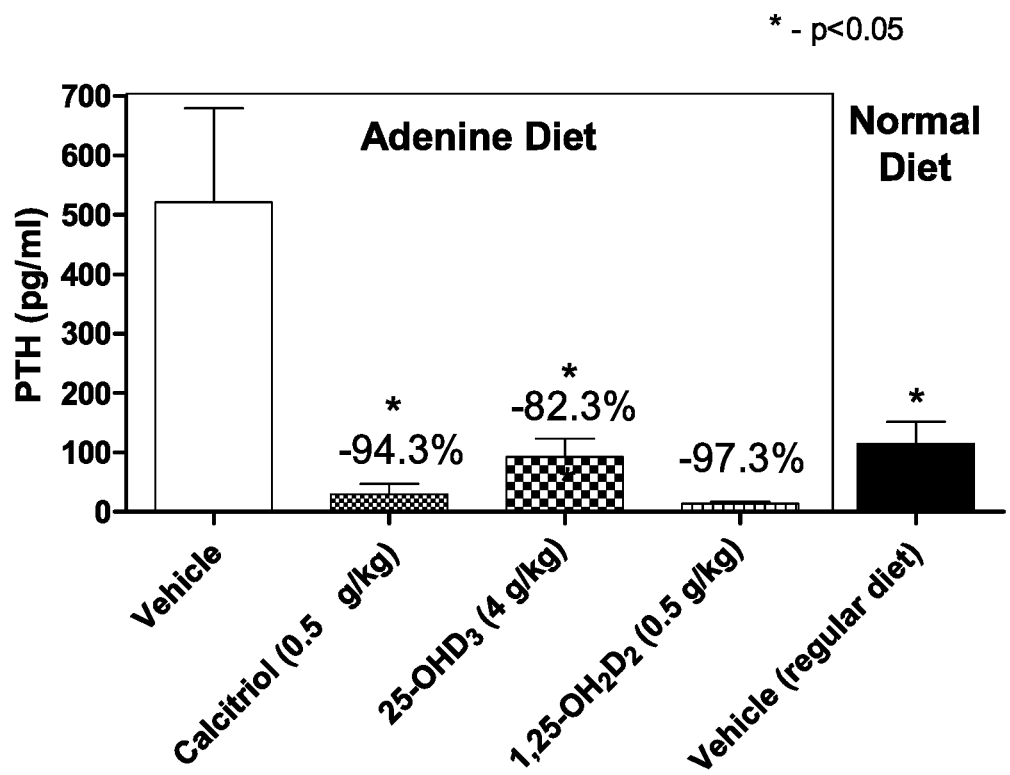
FIG. 2 shows a graph of serum parathyroid hormone (PTH) levels in adenine-fed rats treated with three different vitamin D compounds for one week.

To obtain an animal model of vitamin D deficiency, rats were fed an adenine-rich diet. After 7 days, elevated parathyroid hormone (PTH) levels were observed by an intact PTH (iPTH) Elisa Kit in adenine-fed animals compared to control-diet animals, and after 29 days, secondary hyperparathyroidism had developed in adenine-fed animals, but not in animals receiving the control diet (FIG. 1). iPTH level was significantly reduced by treatment of adenine-fed animals with vitamin D compounds. As shown in FIG. 2, iPTH level in adenine-fed animals was restored to a level similar to control-fed animals by treating the adenine-fed animals with 1,25-(OH)$_2$-$D_3$ (calcitriol or 1,25-dihydroxyvitamin $D_3$), 25-OH-$D_3$ (calcidiol or 25-hydroxyvitamin $D_3$), or 1,25-(OH)$_2$-$D_2$ (1,25-dihydroxyvitamin $D_2$).

Figure 3:
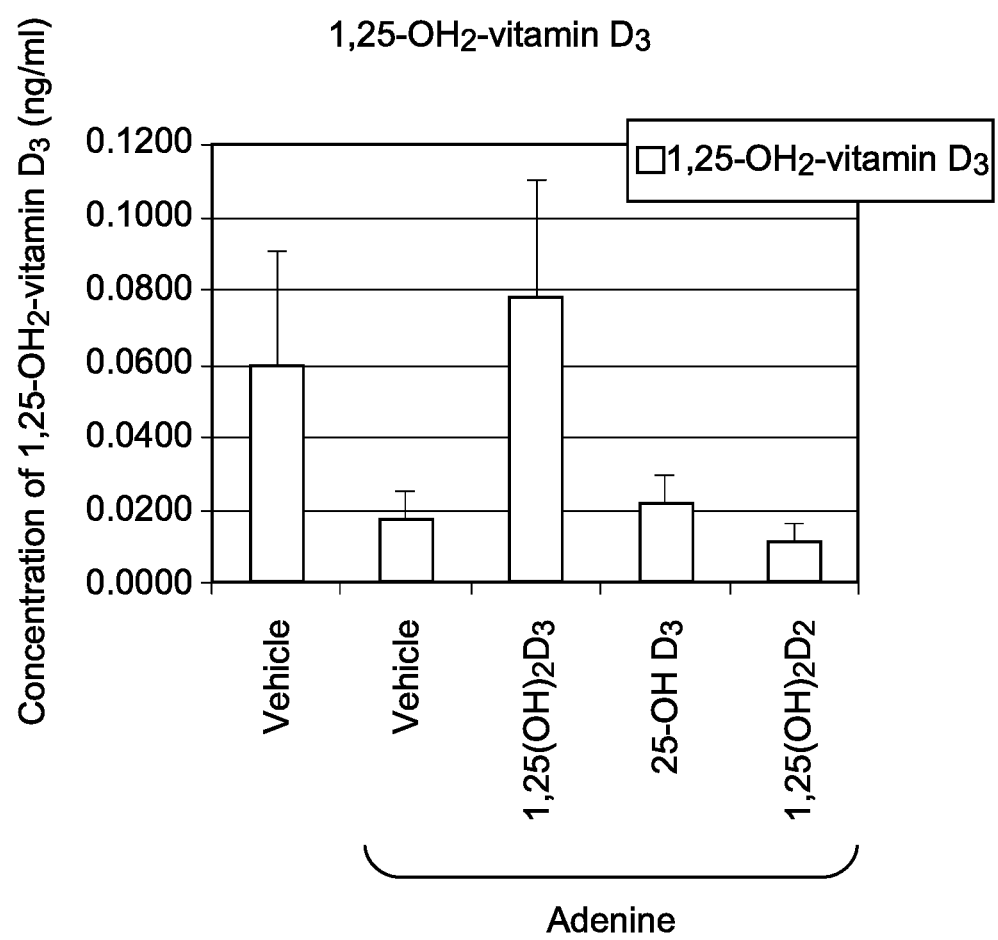
FIG. 3 shows a graph of 1,25-$(OH)_2$-$D_3$ (calcitriol) levels in adenine-fed and control-diet-fed rats and in adenine-fed animals treated with three different vitamin D compounds.

Vitamin D hormone status of the adenine-fed and control animals was assessed by measuring the level of 1,25-(OH)$_2$-$D_3$ (calcitriol or 1,25-dihydroxyvitamin $D_3$), the active form of vitamin D by mass spectrometry. Adenine-fed animals displayed a reduction in vitamin D hormone status compared to animals fed a control diet (FIG. 3). Vitamin D status in adenine-fed animals was restored to the level of control-fed animals by treating the adenine-fed animals with 1,25-(OH)$_2$-$D_3$. In contrast, treatment of adenine-fed animals with 25-OH-$D_3$ (calcidiol or 25-hydroxyvitamin $D_3$) or 1,25-(OH)$_2$-$D_2$ (1,25-dihydroxyvitamin $D_2$) did not significantly affect the 1,25-(OH)$_2$-$D_3$ levels of these animals (FIG. 3).

Example 2

CYP24 Expression in Vitamin D Deficiency

Figure 4:
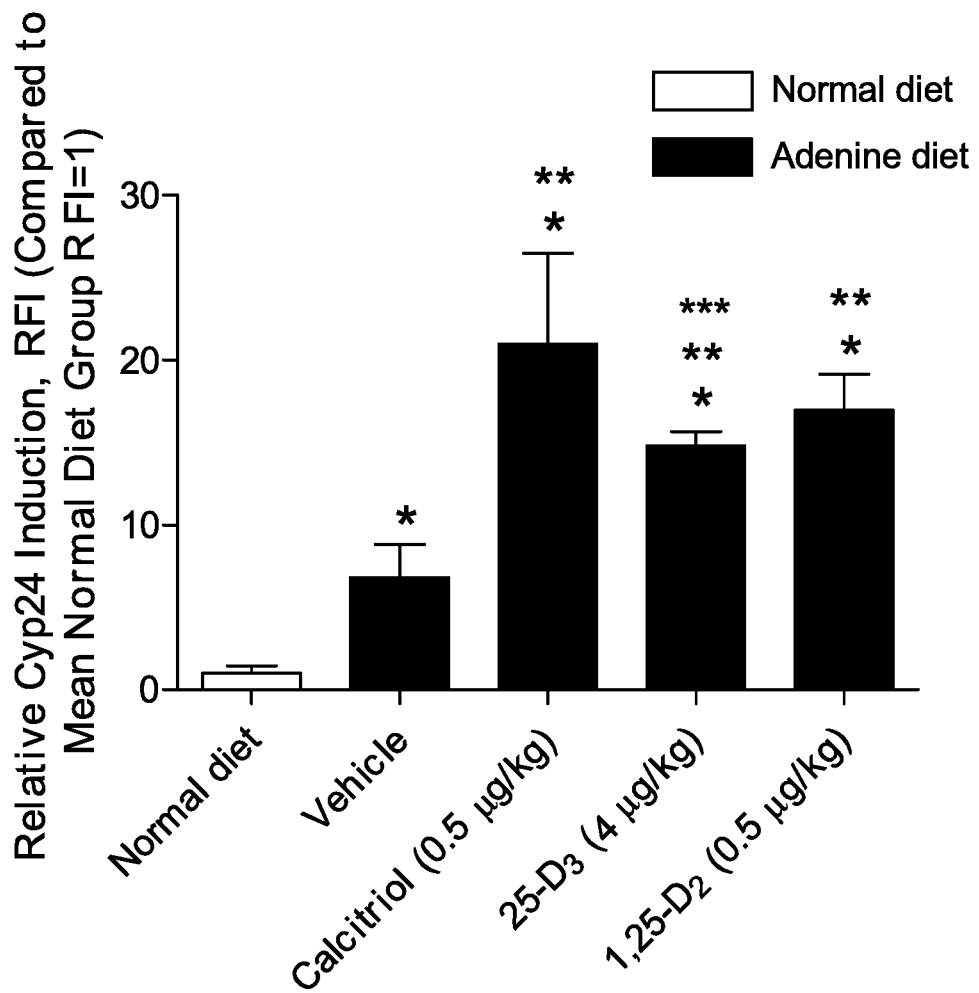
FIG. 4 shows a graph of CYP24 expression in kidney tissue from adenine-fed and control-diet fed rats and from adenine-fed animals treated with three different vitamin D compounds. RFI indicates the relative fold induction.
Figure 5:
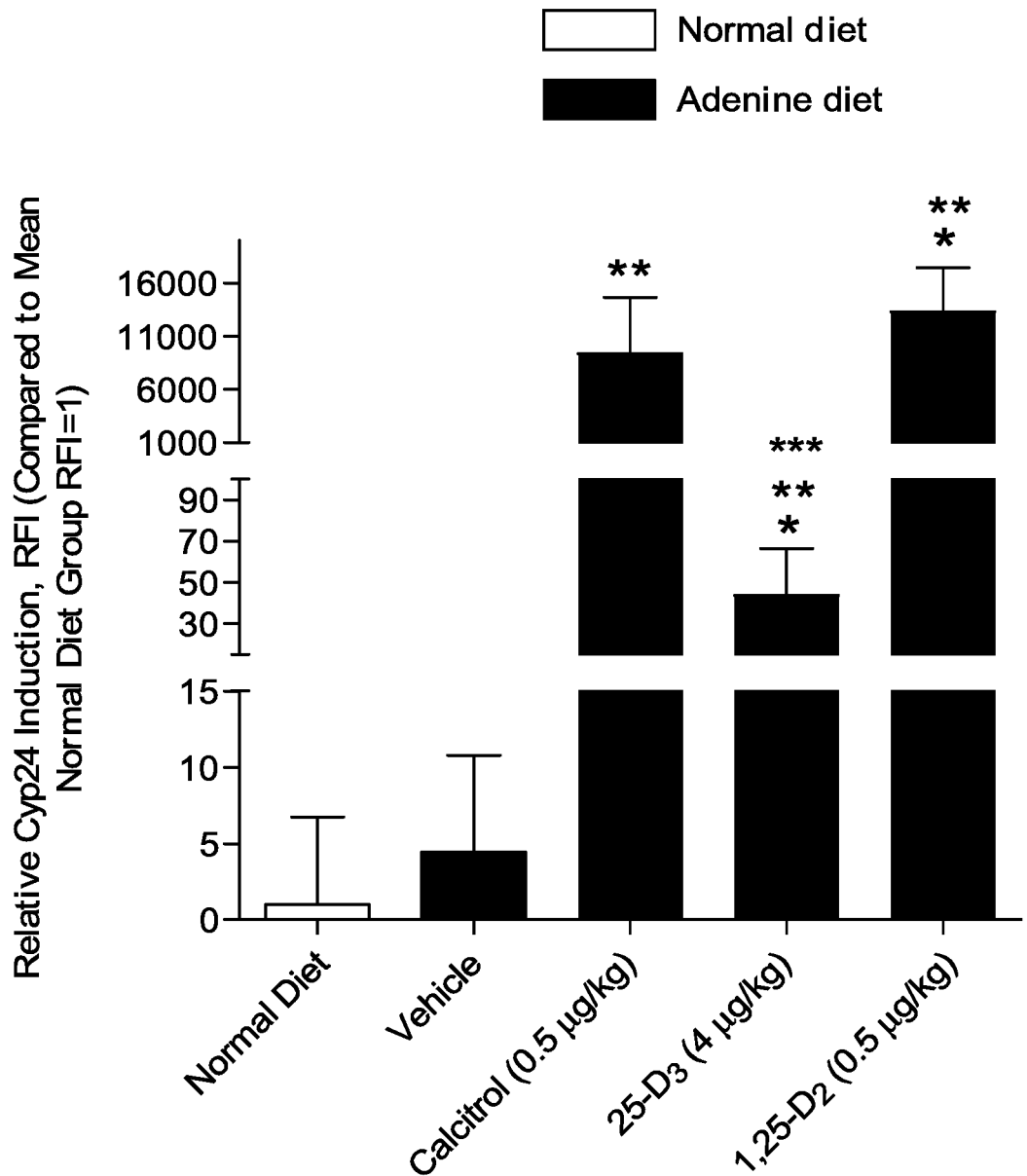
FIG. 5 shows a graph of CYP24 expression in parathyroid gland tissue from adenine-fed and control-diet fed rats and from adenine-fed animals treated with three different vitamin D compounds.

To determine the relationship between vitamin D deficiency and CYP24 level, CYP24 expression was measured by qRT-PCR in adenine-fed rats and control-diet-fed animals. In kidney tissue of adenine-fed animals, CYP24 expression was abnormally elevated approximately 7-fold compared to kidney tissue of control-diet fed animals (FIG. 4). Treatment of adenine-fed animals with vitamin D compounds further induced CYP24. As shown in FIG. 4, treatment of adenine-fed rats with 1,25-(OH)$_2$-D$_3$ (calcitriol or 1,25-dihydroxyvitamin D$_3$), 25-OH-D$_3$ (calcidiol or 25-hydroxyvitamin D$_3$), or 1,25-(OH)$_2$-D$_2$ (1,25-dihydroxyvitamin D$_2$) resulted in 2-fold to 25-fold elevation of CYP24 expression activity. In parathyroid gland tissue of adenine-fed animals, CYP24 expression activity was abnormally elevated approximately 3-fold compared to parathyroid gland tissue of control-diet fed animals (FIG. 5). Treatment of adenine-fed animals with vitamin D compounds dramatically induced CYP24. As shown in FIG. 5, treatment of adenine-fed rats with 1,25-(OH)$_2$-D$_3$ (calcitriol or 1,25-dihydroxyvitamin D$_3$), 25-OH-D$_3$ (calcidiol or 25-hydroxyvitamin D$_3$), or 1,25-(OH)$_2$-D$_2$ (1,25-dihydroxyvitamin D$_2$) resulted in 50-fold to 14,000-fold elevation of CYP24 expression activity.

Example 3

FGF23 Expression in Vitamin D Deficiency

Figure 6:
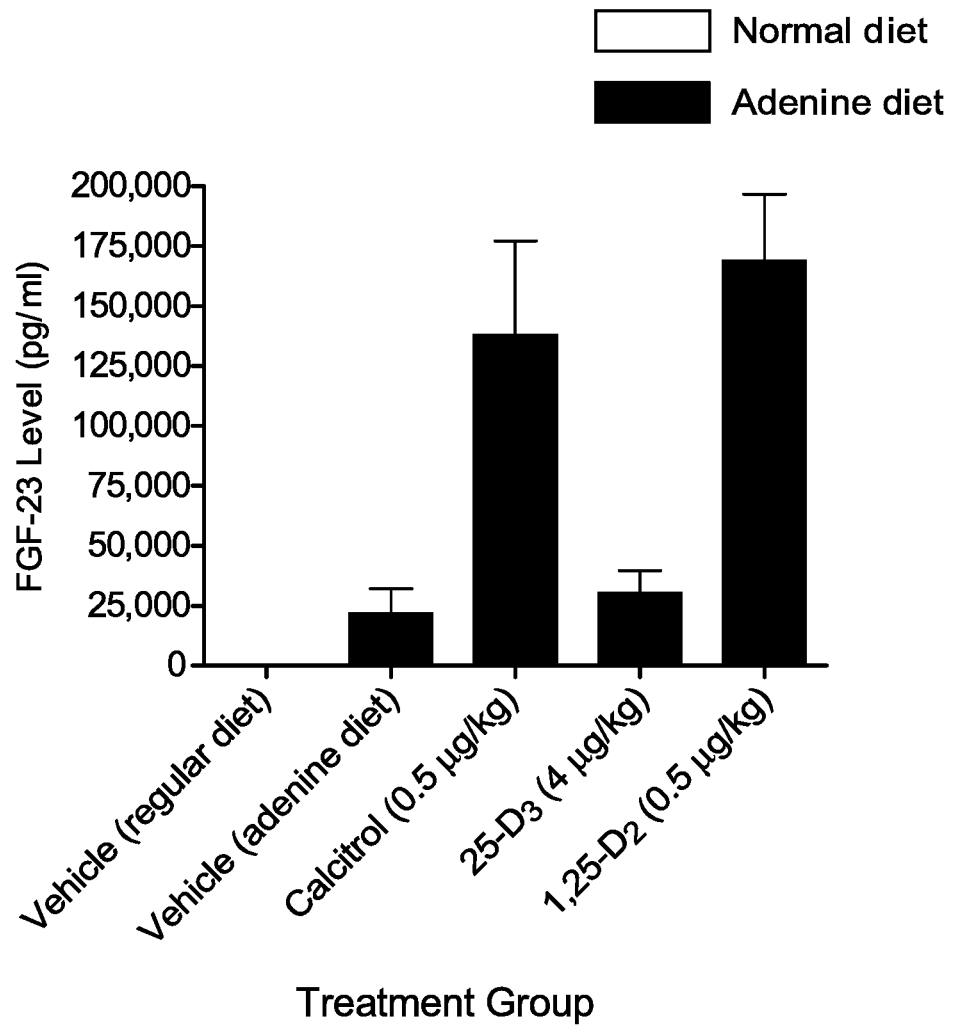
FIG. 6 shows a graph of serum FGF23 levels in adenine-fed and control-diet fed rats and in adenine-fed animals treated with three different vitamin D compounds.

To determine the relationship between vitamin D deficiency and fibroblast growth factor-23 (FGF23) level, serum FGF23 level was measured in adenine-fed rats and control-diet fed animals. In adenine-fed animals, serum FGF23 level was abnormally elevated at least 53-fold compared to control-diet fed animals (FIG. 6). Adenine-fed animals treated with vitamin D compounds also showed elevated levels of FGF23. As shown in FIG. 6, treatment of adenine-fed rats with 1,25-(OH)$_2$-D$_3$ (calcitriol or 1,25-dihydroxyvitamin D$_3$), 25-OH-D$_3$ (calcidiol or 25-hydroxyvitamin D$_3$), or 1,25-(OH)$_2$-D$_2$ (1,25-dihydroxyvitamin D$_2$) resulted in at least 74-fold elevation of FGF23 levels compared to control-diet fed animals.

Figure 7:
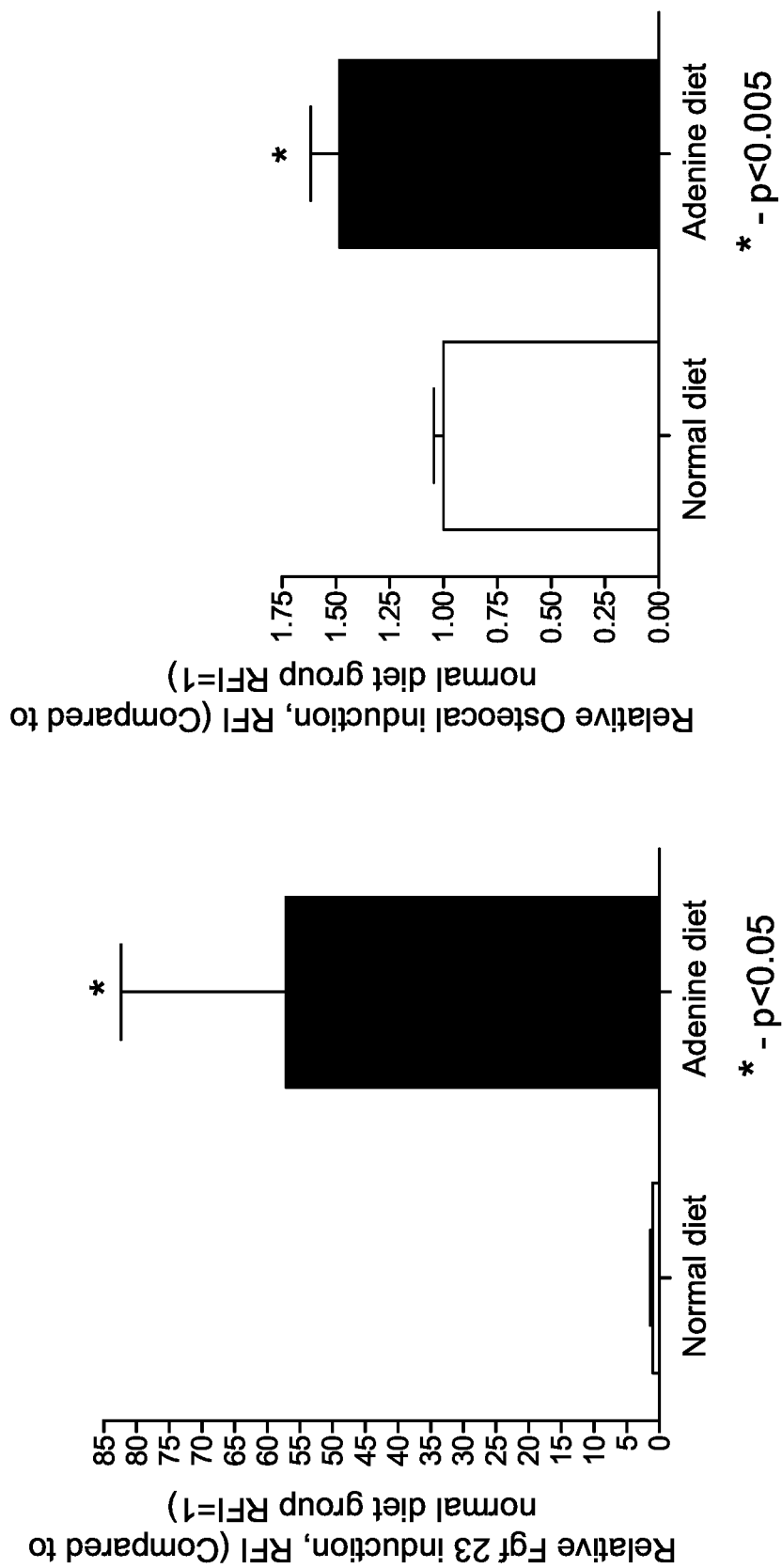
FIG. 7 shows a graph of FGF23 levels and osteoclacin levels in kidney tissue from adenine-fed and control-diet fed rats.

Levels of FGF23 and osteoclacin, a biomarker for bone formation, were measured in kidney tissue from adenine-fed rats and control-diet fed animals. FGF23 was elevated approximately 55-fold and osteoclacin was elevated approximately 1.5-fold in adenine-fed animals compared to control-diet animals (FIG. 7).

Example 4

CYP24 Expression in 25-Hydroxyvitamin D Treatment

Figure 8:
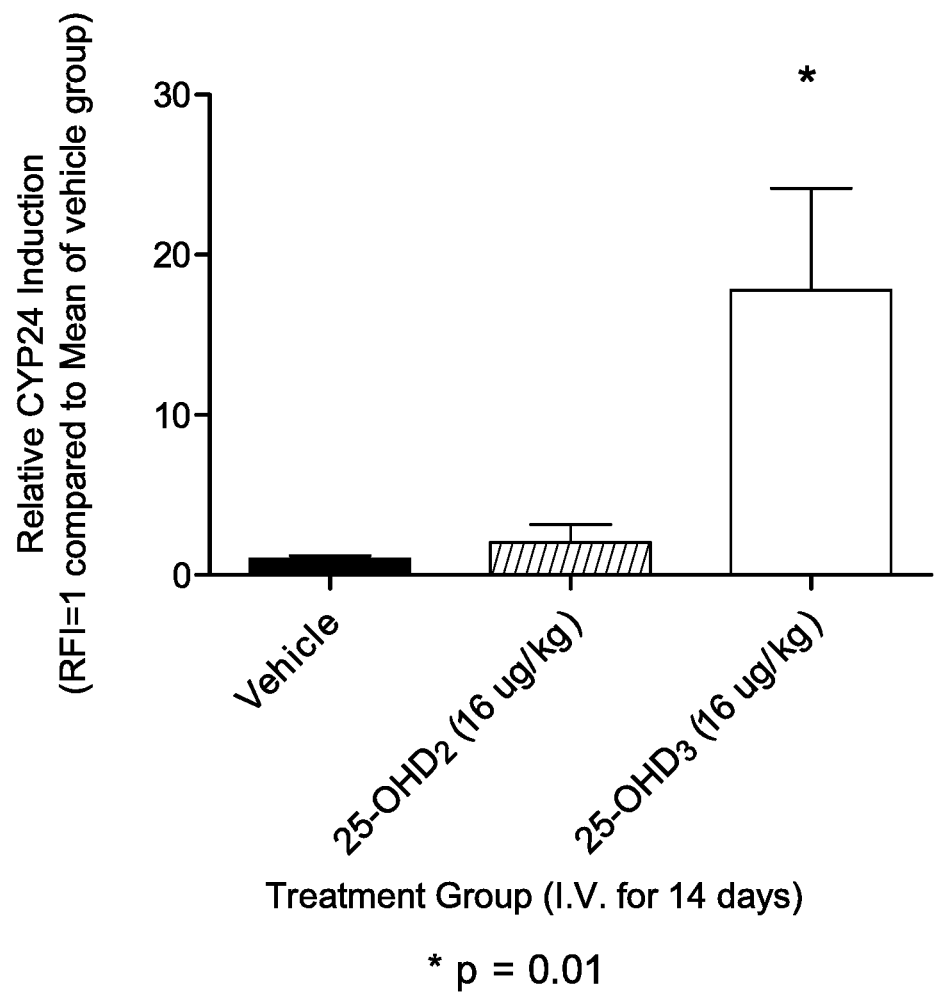
FIG. 8 shows a graph of relative CYP24 induction in rats treated with vitamin D (25-hydroxyvitamin $D_2$ and 25-hydroxyvitamin $D_3$) for 2 weeks.

FIG. 8 shows a graph of relative CYP24 induction in rats treated with vitamin D (25-hydroxyvitamin D$_2$ and 25-hydroxyvitamin D$_3$) for 2 weeks. Normal rats were intravenously administered 16 μg/kg 25-hydroxyvitamin D$_2$, 25-hydroxyvitamin D$_3$, and a control vehicle for 2 weeks. Blood was collected and CYP24 expression was measured by real-time PCR.

Example 5

Figure 9:
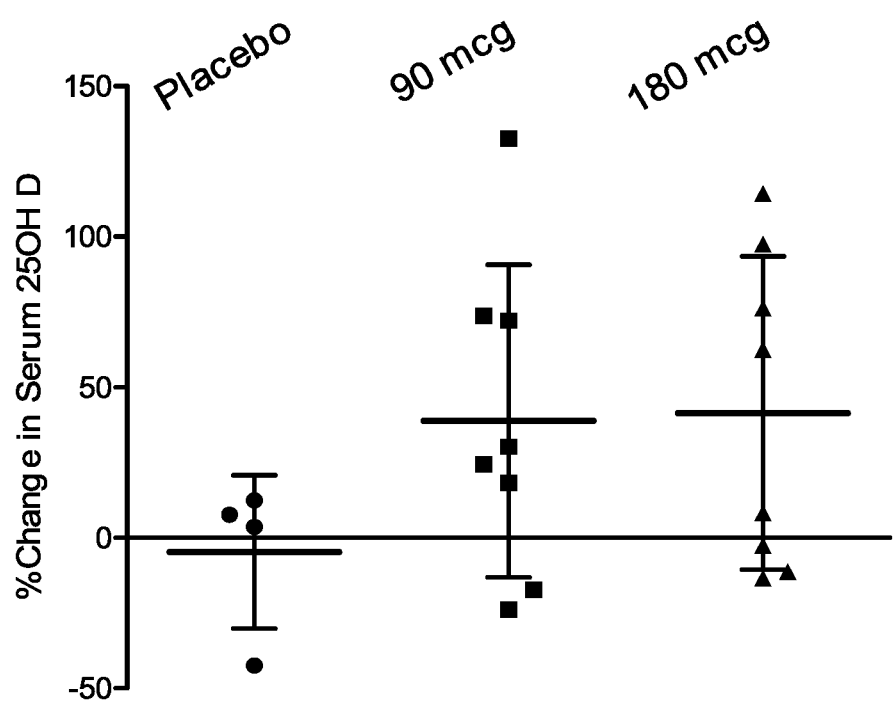
FIG. 9 shows changes 25-OH-D levels in humans in response to administration of placebo and (5Z,7E,16Z,23E)-(1S,3R)-25-nor-25-t-butylsulfonyl-9,10-seco-5,7,10(19),16,23-cholestapentaene-1,3-diol.

The effect of 5Z,7E,16Z,23E)-(1S,3R)-25-nor-25-t-butylsulfonyl-9,10-seco-5,7,10(19),16,23-cholestapentaene-1,3-diol on 25-hydroxyvitamin D levels was assessed in human subjects. Subjects were dosed with placebo or the compound on days 1, 3, 5, 8, and 10. Twenty-four hours after the last dose of the compound, 25-hydroxyvitamin D level was measured. The percent change in serum 25-hydroxyvitamin D is shown in FIG. 9 (p=0.1 for both 90 mcg and 180 mcg).

Example 6

Sprague-Dawley rats were treated i.v. daily with vehicle or 0.5 mcg/kg 1,25-dihydroxyvitamin D$_3$ for 1 week. Organs were collected 24 hours after the last dosing. CYP24 gene expression was determined by real-time PCR. The results are shown in FIG. 10.

Sprague-Dawley rats were fed a standard diet (normal) or a uremia-inducing diet containing 0.75% adenine (uremic) for 4 weeks. Animals were then dosed i.v. daily with vehicle or 0.5 mcg/kg 1,25-dihydroxyvitamin D$_3$ for 7 days. Organs were collected 24 hours after the final dosing. CYP24 gene expression was determined by real-time PCR and normalized to GAPDH levels. Relative expression values are normalized to the vehicle-treated group (relative expression=1). The results are shown in FIG. 11.

Figure 10:
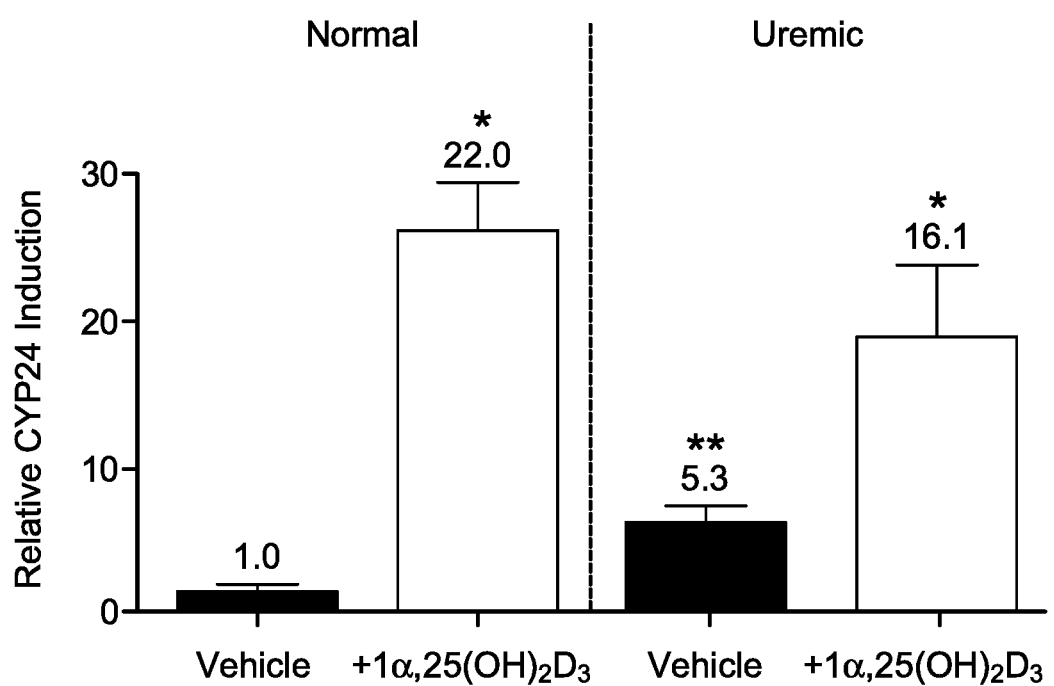
FIG. 10 shows relative CYP24 induction in kidney tissue in normal and adenine-induced uremic rats, showing that basal expression of CYP24 (vehicle) and induced expression of CYP24 by 1,25-dihydroxyvitamin $D_3$ (1α,25$(OH)_2D_3$).
Figure 11:
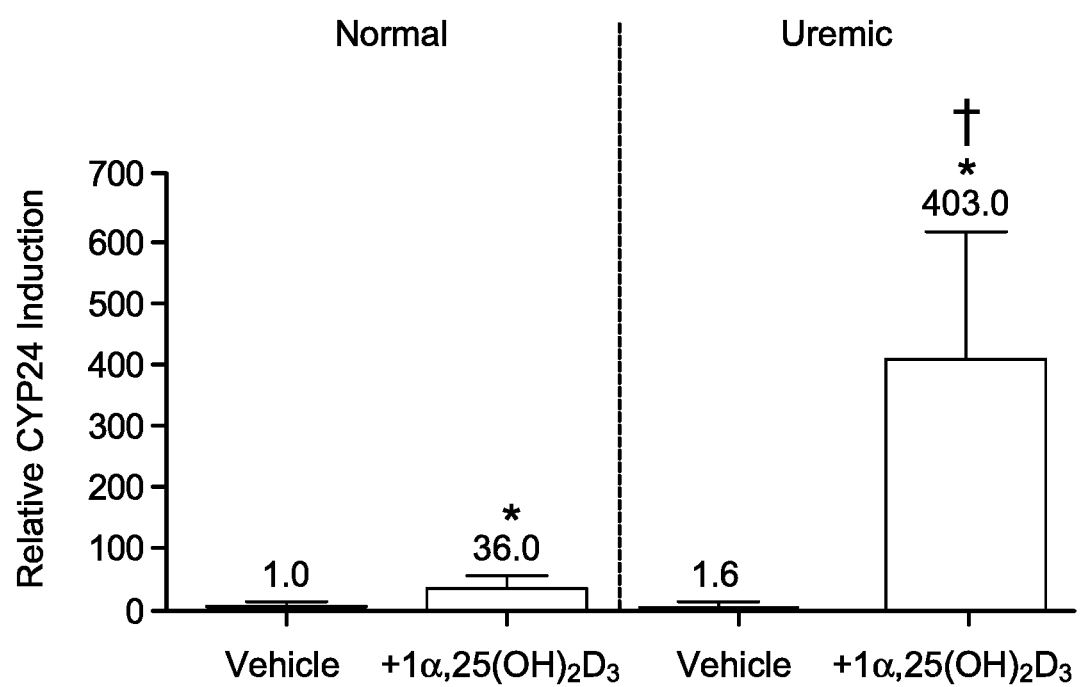
FIG. 11 shows relative CYP24 induction in parathyroid gland tissue in normal and adenine-induced uremic rats, showing that basal expression of CYP24 (vehicle) and induced expression of CYP24 by 1,25-dihydroxyvitamin $D_3$ (1α,25$(OH)_2D_3$).

FIGS. 10 and 11 show that basal expression of CYP24 is significantly elevated in kidney (FIG. 10), but not parathyroid gland (FIG. 11), in the uremic rat compared to the normal rat. However, induced expression of CYP24 by 1,25-dihydroxyvitamin D$_3$ (1α,25(OH)$_2$D$_3$) is markedly greater in parathyroid gland from uremic compared to normal animals. "*" denotes a significant difference in CYP24 expression between vehicle and 1,25-dihydroxyvitamin D$_3$ treatment in normal and uremic rats. "**" represents a significant difference between vehicle-treated normal and uremic rats. "+" denotes significant difference in CYP24 induction levels between normal and uremic rats treated with 1,25-dihydroxyvitamin D$_3$. Significance was set at a p value cutoff of <0.05. Data are presented as mean±SEM. Numerals above each bar signifies relative fold induction to normal-vehicle.

Example 7

CYP24 and CYP27B1 expression was measured using the same protocol outlined above in Example 6 with respect to FIG. 11. Serum levels of 25(OH)D$_3$ and 1,25-dihydroxyvitamin D$_3$ were measured by LC-MS. Serum PTH was measured by ELISA IMMUTOPICS (San Clemente, Calif., USA) according to manufacturer's instructions. Briefly, serum samples were spiked with [26,27-$^2$H$_6$] 25(OH)D$_3$ or [25,26-$^2$H$_6$] 1,25-dihydroxyvitamin D$_3$ and dissolved in acetonitrile to serve as an internal standard. 1,25-dihydroxyvitamin D$_3$ or 25(OH)D$_3$ and internal standards were extracted from serum using Accubond II ODS-C18 100 mg, 1 mL SPE cartridges (Agilent Technologies). The collected fractions were evaporated to dryness under a steady stream of nitrogen gas and the residues reconstituted in 50 μL of methanol/H$_2$O (80/20; v/v) and analyzed using LC-MS/MS (Waters Alliance HPLC—Waters Quattro Ultima mass spectrometer). Relative expression values are normalized to the vehicle-treated group (relative expression=1). The results are shown in FIG. 12.

FIG. 12 shows that increased basal CYP24 expression, in the absence of changes to CYP27B1, may contribute to lower levels of 1,25-dihydroxyvitamin D$_3$ in uremic rats. Treatment with 1,25-dihydroxyvitamin D$_3$ causes a reduction in serum 25-(OH)D$_3$ levels. Treatment with 1,25-dihydroxyvitamin D$_3$ causes a reduction in PTH, but also drastically induces CYP24 expression. Asterisk represents a statistically significant difference between normal and uremic groups for CYP27B1 (*) and CYP24 (**). In the upper panel, (*) denotes a significant difference in vitamin D levels between normal and uremic rats. Statistical significance was determined using student's independent t test with p value cut off of <0.05. Data are presented as mean±SEM.

Example 8

Vitamin D deficiency was induced in Sprague-Dawley rats by feeding a diet lacking vitamin D for 6 weeks. Normal rats were fed a standard diet containing vitamin D. Uremia was induced by oral administration (gavage) of 0.2% adenine solution for the last 2 weeks. Non-uremic controls rats were administered vehicle by oral gavage. Serum and organs were collected 24 hours after the last dose of adenine. Gene expression was determined by real-time PCR. Measurement of serum levels of 25(OH)$D_3$ and 1,25-dihydroxyvitamin $D_3$ is detailed above with respect to Example 7. The results are shown in FIG. 13.

Figure 13:
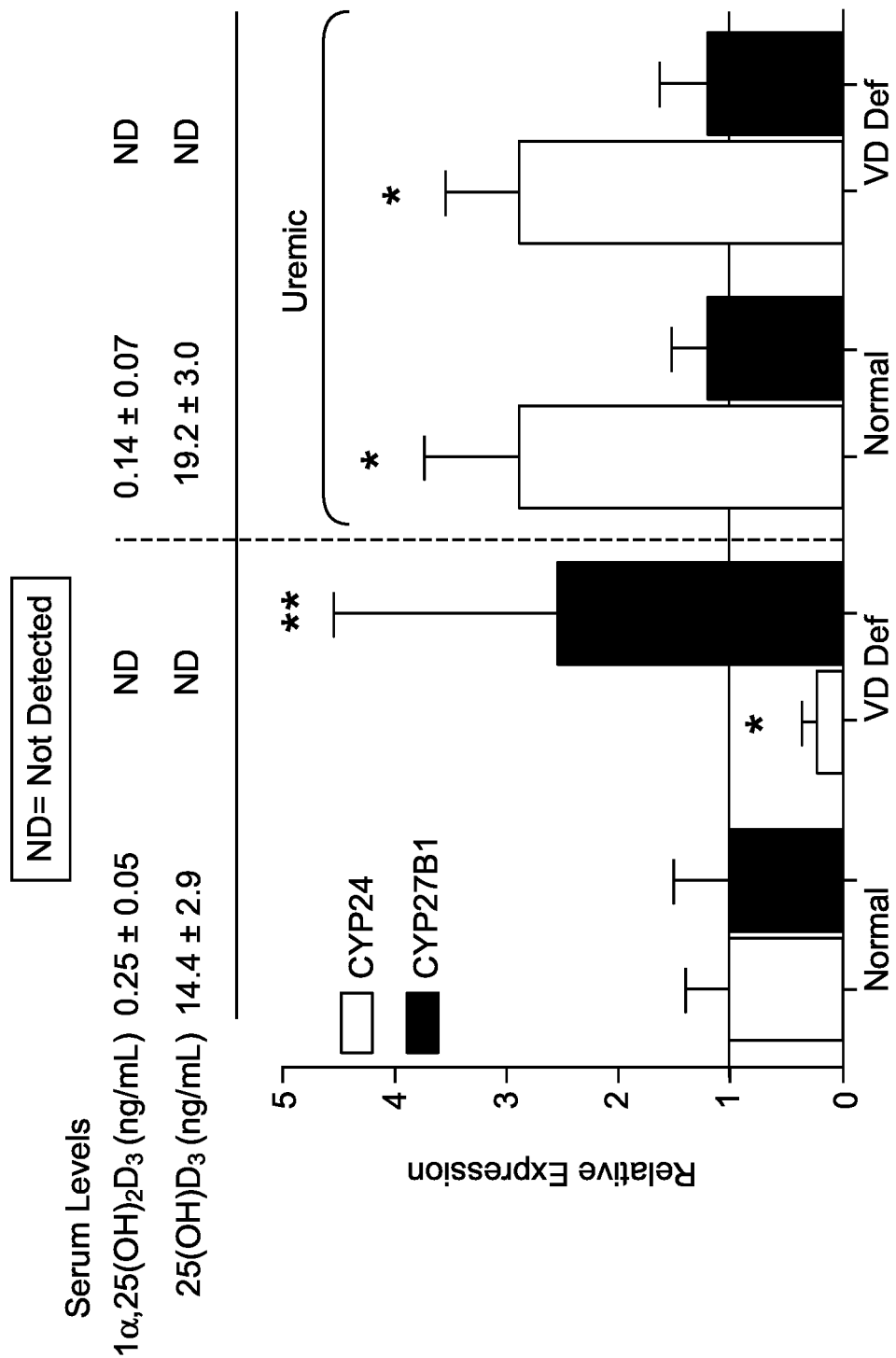
FIG. 13 shows relative expression of CYP24 and CYP27B1 in normal rats versus normal rats on a vitamin-D deficient diet, and between adenine-induced uremic rats on a normal diet and on a vitamin-D deficient diet.

FIG. 13 shows that increased basal expression of CYP24 is not dependent on vitamin D metabolite levels in uremic rats. "*" denotes a significant difference between groups relative to non-uremic normal. "**" represents a significant difference between CYP27B1 normal and CYP27B1 vitamin D deficient (VD Def) diet. Statistical significance was determined using student's independent t test with p value cut off of <0.05. Data are presented as mean±SEM. Non-detectable levels are designated as "ND."

Example 9

Figure 14:
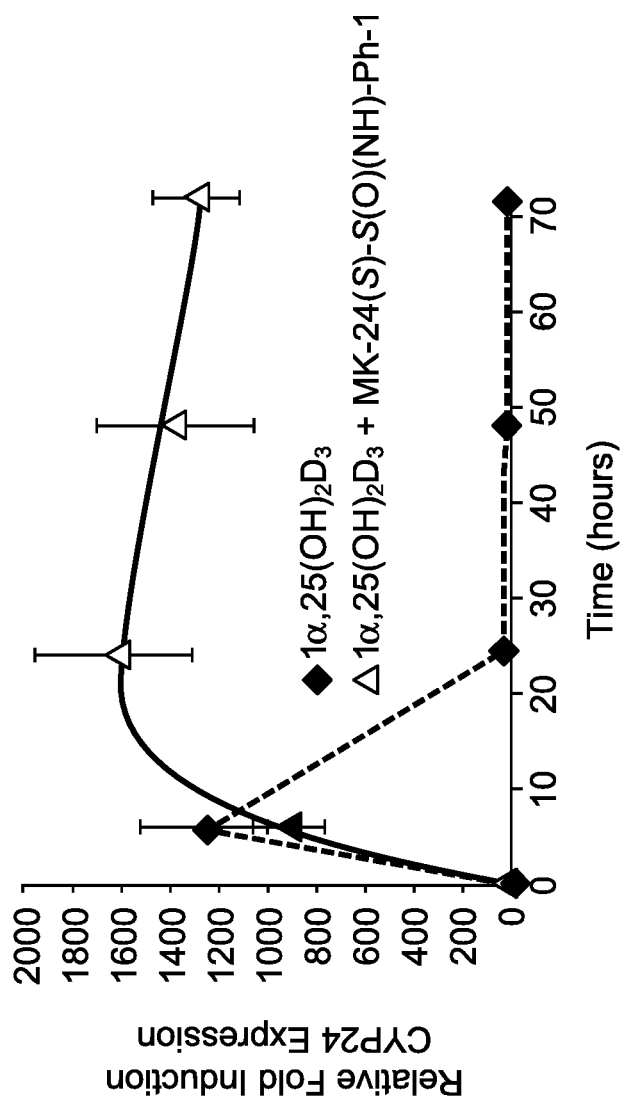
FIG. 14 shows relative induction of CYP24 expression in HEK cells incubated with 1,25-dihydroxyvitamin $D_3$ alone or with a CYP24 inhibitor.

HEK cells were seeded at 25,000 cells per well (24-well plate) and incubated with 1,25-dihydroxyvitamin $D_3$ (10 nM) alone or with a CYP24 inhibitor (MK-24(S)—S(O)(NH)-Ph-1, see U.S. Pat. No. 7,101,865, compound I(a)) (10 nM) for 6, 24, 48 and 72 hours. Cells were collected and RNA was prepared using TRIZOL® reagent. CYP24 was quantified using real-time PCR. The results are shown in FIG. 14.

The results show that CYP24 induction is markedly extended by 1,25-dihydroxyvitamin $D_3$ in the presence of CYP24 inhibitor MK-24(S)—S(O)(NH)-Ph-1.

Example 10

Figure 15:
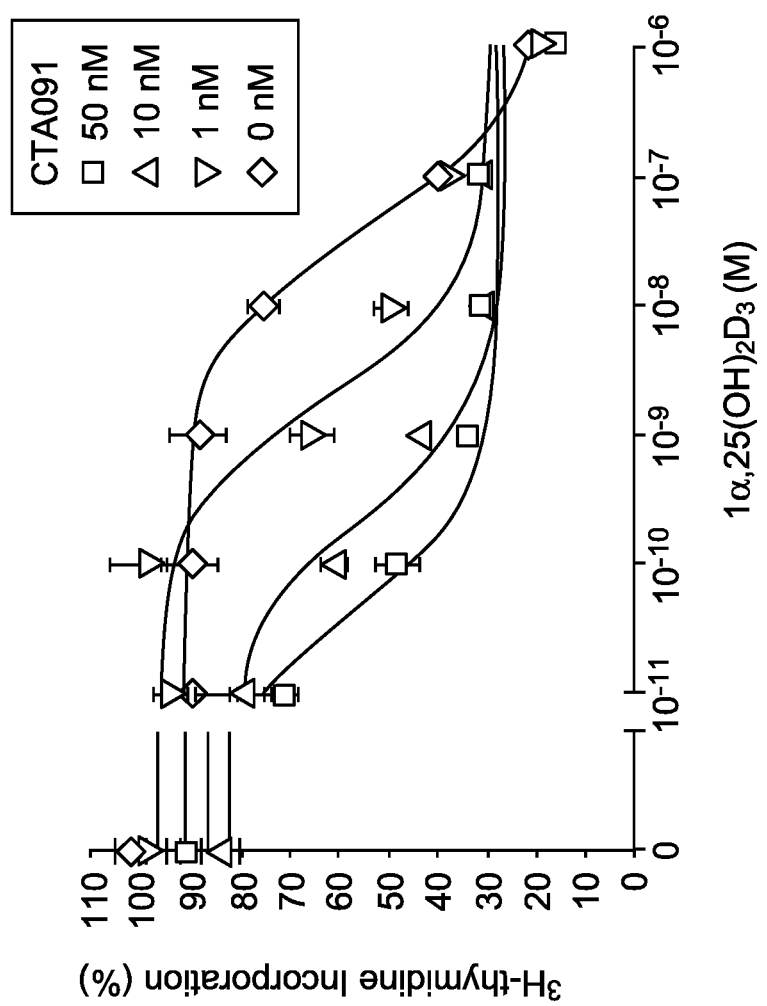
FIG. 15 shows the 3H-thymidine incorporation (%) in HEK cells treated with 1,25-dihydroxyvitamin $D_3$ alone or in combination with a CYP24 inhibitor at various concentrations.

HEK cells were transferred into 96-well plates at 2000 cells/well density. After 2 days of growth in 96-well plates the cells were treated with 1,25-dihydroxyvitamin $D_3$ at the final concentrations $10^{-6}$-$10^{-11}$ M in combination with the MK-24(S)—S(O)(NH)-Ph-1 compound with the varied final concentration of 0, 1, 10 and 50 nM. After overnight treatment [$^3$H]-thymidine was added to cells, 0.2 mCi/well in KGM media for 16 h. The radioactivity incorporation was counted using a scintillation counter after the addition of 25 ml of scintillation fluid. The results are shown in FIG. 15. The data were represented as an incorporation of thymidine in cpm depending on 1,25-dihydroxyvitamin $D_3$ concentration. Each data point represents at least 4 independent trials.

The results show that inhibition of CYP24 activity enhances the anti-proliferative effects of 1,25-dihydroxyvitamin $D_3$ in cultured HEK cells approximately 3 orders of magnitude.

Example 11

Figure 16:
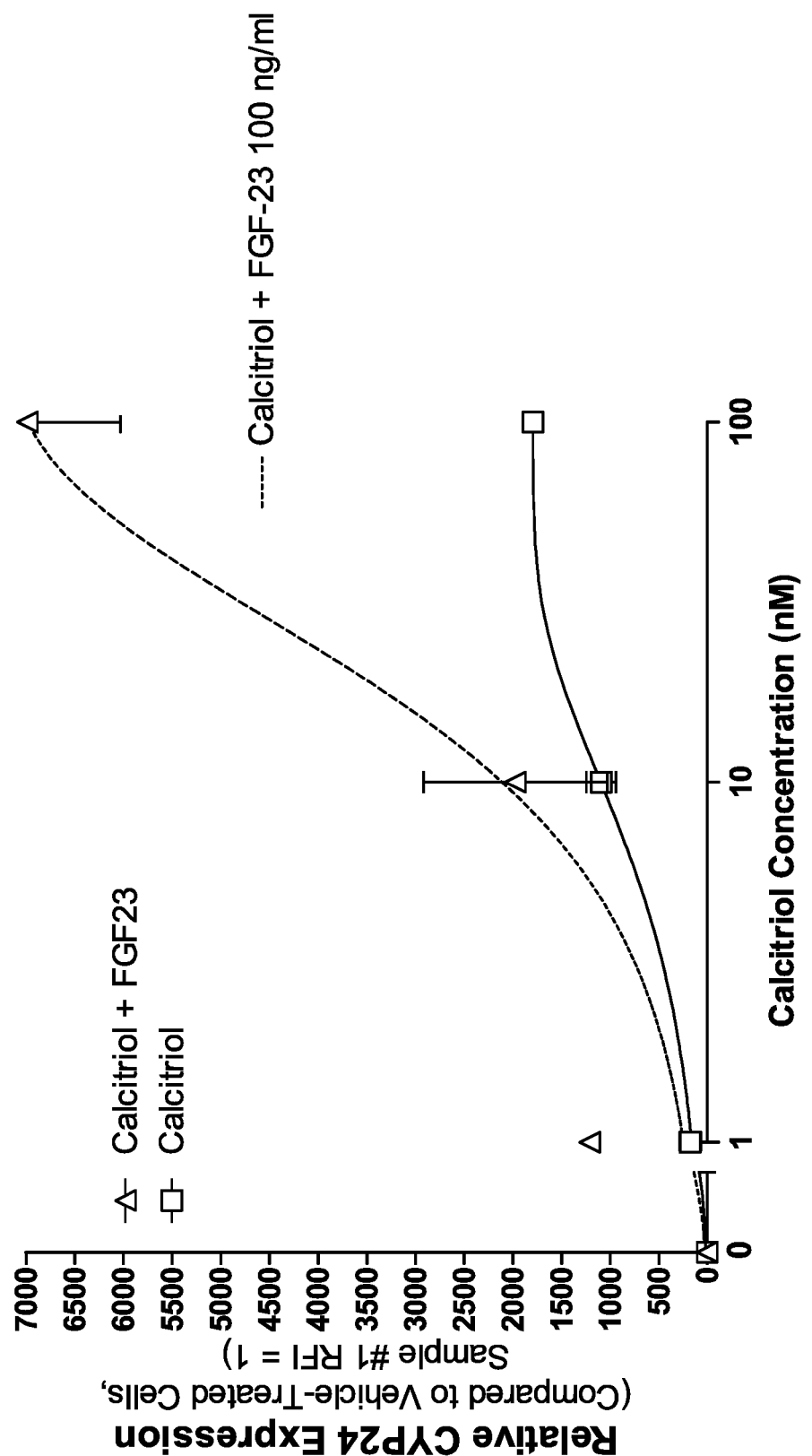
FIG. 16 shows the relative expression of CYP24 in HPK1a-ras cells treated with 1,25-dihydroxyvitamin $D_3$ alone or in combination with FGF23.

HPK1a-ras cells were treated with 0, 1, 10, and 100 nM of 1,25-dihydroxyvitamin $D_3$ (calcitriol), with or without 100 ng/mL of FGF23, and CYP24 RNA expression was measured after 8 hours. The results show that the presence of FGF23 synergizes with 1,25-dihydroxyvitamin $D_3$ to induce CYP24 RNA production (FIG. 16).

Example 12

Figure 17:
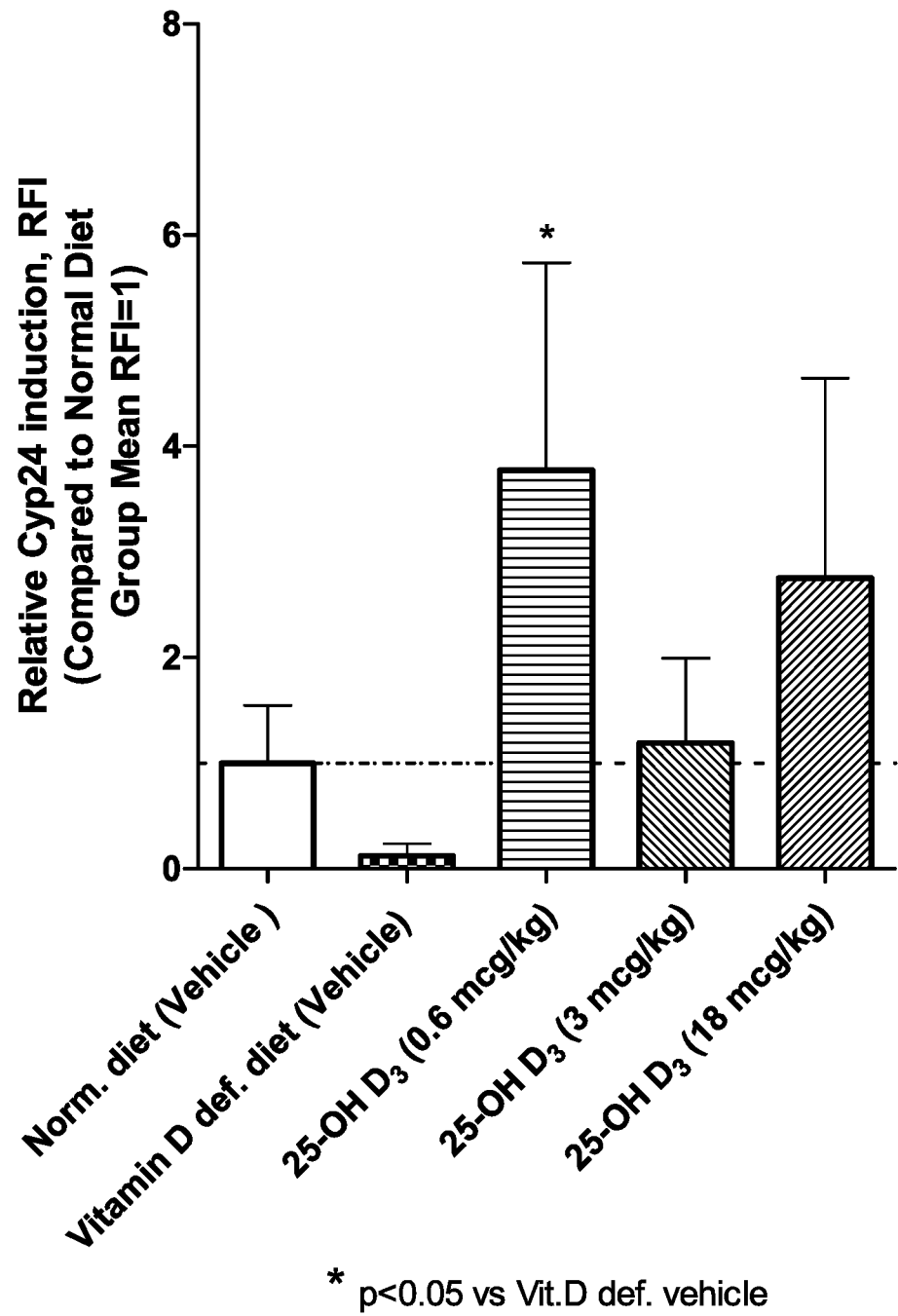
FIG. 17 shows the relative induction of CYP24 in normal rats versus normal rats fed a vitamin D deficient diet, and normal rats fed a vitamin D deficient diet that were treated with various concentrations of 25-hydroxyvitamin $D_3$.

Sprague Dawley rats were fed either a normal diet or a vitamin D deficient diet for a period of four weeks. Animals were then injected daily for two weeks with either 25-hydroxyvitamin $D_3$ at 0.6, 3, or 18 mcg/kg or vehicle as per the axis label in FIG. 17. Kidneys were collected 24 hours after the last injection and CYP24 mRNA levels were measured by real-time PCR. Results are shown in FIG. 17.

Example 13

Figure 18:
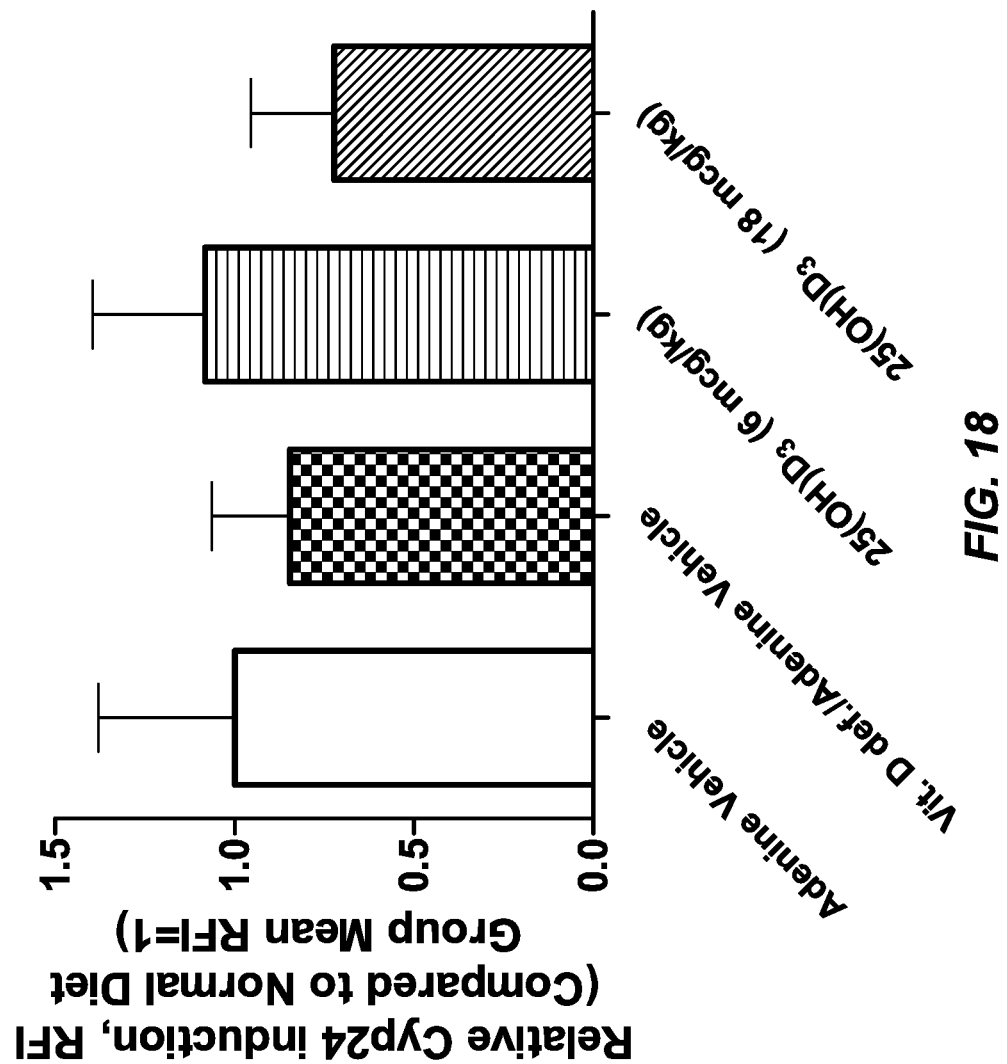
FIG. 18 shows the relative induction of CYP24 in rats fed a normal diet supplemented with adenine ("Adenine Vehicle") versus a vitamin D deficient diet supplemented with adenine and versus rats fed a vitamin D deficient diet supplemented with adenine and treated with various concentrations of 25-hydroxyvitamin $D_3$.

Sprague Dawley rats were fed either a normal diet (Adenine Vehicle group) or a vitamin D deficient diet (Vit. D def./Adenine Vehicle group) for a period of four weeks. Following this treatment, animals were orally administered, daily for two weeks, 100 mg of adenine. Animals were then injected daily for another two weeks with either 25-hydroxyvitamin $D_3$ at 0.6 or 18 mcg/kg or vehicle as per the axis label in FIG. 18. Kidneys were collected 24 hours after the last injection and CYP24 mRNA levels were measured by real-time PCR. Results are shown in FIG. 18.

Example 14

Figure 19:
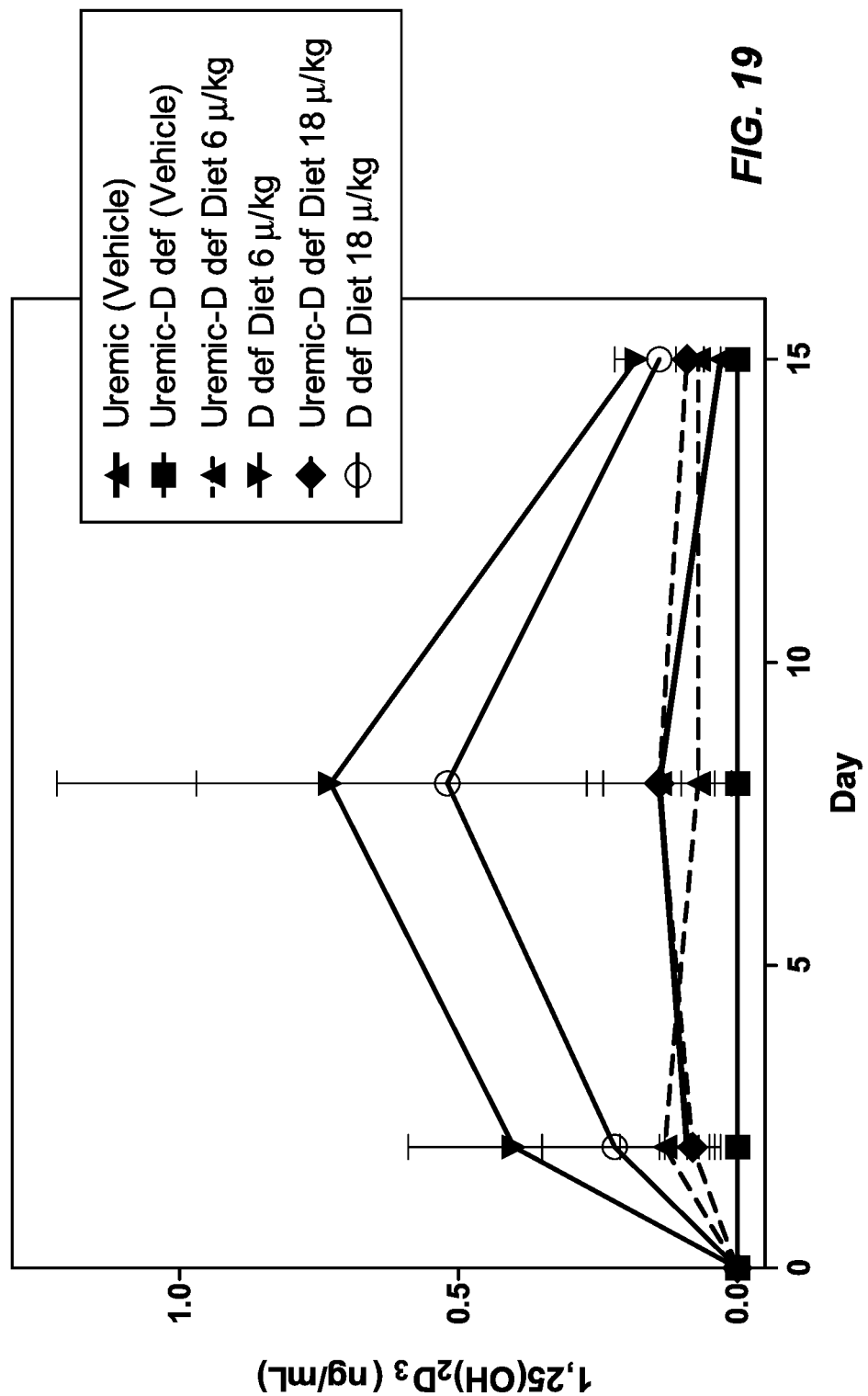
FIG. 19 shows the effect of 25-hydroxyvitamin $D_3$ on the concentration of 1,25-dihydroxyvitamin $D_3$ in uremic vitamin D deficient rats versus otherwise normal vitamin D deficient rats.

FIG. 19 shows the levels of 1,25-dihydroxyvitamin $D_3$ in vitamin D deficient uremic rats compared to vitamin D deficient rats that were dosed with 6 or 18 mcg/kg of 25-hydroxyvitamin D for two weeks.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

All patents, publications and references cited herein are hereby fully incorporated by reference. In case of conflict between the present disclosure and incorporated patents, publications and references, the present disclosure should control.

What is claimed is:

1. An extended release pharmaceutical formulation comprising a CYP24 inhibitor and a vitamin D prohormone.

2. The formulation of claim 1, wherein the CYP24 inhibitor is a pure inhibitor of CYP24 or a dual-action CYP24 inhibitor/VDR agonist.

3. The formulation of claim 1, wherein the CYP24 inhibitor is selected from 23,23-difluoro-24-sulfone vitamin $D_3$ compounds, 25-sulfone vitamin $D_3$ compounds, 24,24-difluoro-25-sulfone vitamin $D_3$ compounds, 24-sulfoximine vitamin $D_3$ compounds, 16-ene-25-oxime vitamin $D_3$ compounds, and 16-ene-25-oxime ether vitamin $D_3$ compounds, 24-sulfone vitamin $D_3$ compounds, and 24,24-difluoro vitamin $D_3$ compounds.

4. The formulation of claim 1, wherein the vitamin D prohormone is selected from 25-hydroxyvitamin $D_2$, 25-hydroxyvitamin $D_3$, and combinations thereof.

5. The formulation of claim 4, wherein the vitamin D prohormone is 25-hydroxyvitamin $D_3$.

6. The formulation of claim 1, wherein the formulation is for oral administration.

7. The formulation of claim 1, further comprising an oil.

8. The formulation of claim 7, further comprising esters of fatty acids.

9. The formulation of claim 8, wherein the esters of fatty acids are fatty acid glycerides.

10. The formulation of claim 1, wherein the formulation comprises a capsule.

11. A method of treating vitamin D deficiency in a patient comprising administering to the patient an effective amount of the formulation of claim 1 to increase to or maintain serum 25-hydroxyvitamin D at a level of at least 30 ng/m L.

12. The method of claim 11, wherein the CYP24 inhibitor is a pure inhibitor of CYP24 or a dual-action CYP24 inhibitor/VDR agonist.

13. The method of claim 11, wherein the CYP24 inhibitor is selected from 23,23-difluoro-24-sulfone vitamin $D_3$ compounds, 25-sulfone vitamin $D_3$ compounds, 24,24-difluoro-25-sulfone vitamin $D_3$ compounds, 24-sulfoximine vitamin $D_3$ compounds, 16-ene-25-oxime vitamin $D_3$ compounds, and 16-ene-25-oxime ether vitamin $D_3$ compounds, 24-sulfone vitamin $D_3$ compounds, and 24,24-difluoro vitamin $D_3$ compounds.

14. The method of claim 11, wherein the vitamin D prohormone is selected from 25-hydroxyvitamin $D_2$, 25-hydroxyvitamin $D_3$, and combinations thereof.

15. The method of claim 14, wherein the vitamin D prohormone is 25-hydroxyvitamin $D_3$.

16. The method of claim 11, wherein the extended release formulation is administered orally.

17. The method of claim 11, wherein the extended release formulation comprises an oil.

18. The method of claim 17, wherein the extended release formulation comprises esters of fatty acids.

19. The method of claim 18, wherein the esters of fatty acids are fatty acid glycerides.

20. The method of claim 11, wherein the extended release formulation comprises a capsule.

21. The method of claim 11, wherein the patient has secondary hyperparathyroidism.

22. The method of claim 11, wherein the patient has Chronic Kidney Disease Stage 1 or Stage 2.

23. The method of claim 11, wherein the patient has Chronic Kidney Disease Stage 3 or Stage 4.

24. The method of claim 11, wherein the patient has Chronic Kidney Disease Stage 5.

25. A method of treating secondary hyperparathyroidism in a patient having Chronic Kidney Disease (CKD) comprising administering an effective amount of the formulation of claim 1 to lower serum parathyroid hormone.

26. The method of claim 25, wherein the CYP24 inhibitor is a pure inhibitor of CYP24 or a dual-action CYP24 inhibitor/VDR agonist.

27. The method of claim 25, wherein the CYP24 inhibitor is selected from 23,23-difluoro-24-sulfone vitamin $D_3$ compounds, 25-sulfone vitamin $D_3$ compounds, 24,24-difluoro-25-sulfone vitamin $D_3$ compounds, 24-sulfoximine vitamin $D_3$ compounds, 16-ene-25-oxime vitamin $D_3$ compounds, and 16-ene-25-oxime ether vitamin $D_3$ compounds, 24-sulfone vitamin $D_3$ compounds, and 24,24-difluoro vitamin $D_3$ compounds.

28. The method of claim 25, wherein the vitamin D prohormone is selected from 25-hydroxyvitamin $D_2$, 25-hydroxyvitamin $D_3$, and combinations thereof.

29. The method of claim 28, wherein the vitamin D prohormone is 25-hydroxyvitamin $D_3$.

30. The method of claim 25, wherein the extended release formulation is administered orally.

31. The method of claim 25, wherein the extended release formulation comprises an oil.

32. The method of claim 31, wherein the extended release formulation comprises esters of fatty acids.

33. The formulation of claim 32, wherein the esters of fatty acids are fatty acid glycerides.

34. The method of claim 25, wherein the extended release formulation comprises a capsule.

35. The method of claim 25, wherein the patient has Chronic Kidney Disease Stage 1 or Stage 2.

36. The method of claim 25, wherein the patient has Chronic Kidney Disease Stage 3 or Stage 4.

37. The method of claim 25, wherein the patient has Chronic Kidney Disease Stage 5.

* * * * *